(12) United States Patent
Ishihara et al.

(10) Patent No.: US 7,504,417 B2
(45) Date of Patent: Mar. 17, 2009

(54) SUBSTITUTED BENZENE DERIVATIVES OR SALTS THEREOF

(75) Inventors: Tsukasa Ishihara, Tsukuba (JP); Fukushi Hirayama, Tsukuba (JP); Keizo Sugasawa, Tsukuba (JP); Yuji Koga, Tsukuba (JP); Takeshi Kadokura, Tsukuba (JP); Takeshi Shigenaga, Tsukuba (JP)

(73) Assignee: Astellas Pharma Inc., Tokyo (JP)

( * ) Notice: Subject to any disclaimer, the term of this patent is extended or adjusted under 35 U.S.C. 154(b) by 307 days.

(21) Appl. No.: 10/399,625

(22) PCT Filed: Nov. 21, 2001

(86) PCT No.: PCT/JP01/10176

§ 371 (c)(1), (2), (4) Date: Sep. 10, 2003

(87) PCT Pub. No.: WO02/42270

PCT Pub. Date: May 30, 2002

(65) Prior Publication Data

US 2004/0077555 A1 Apr. 22, 2004

(30) Foreign Application Priority Data

Nov. 22, 2000 (JP) ............................. 2000-356146
Dec. 22, 2000 (JP) ............................. 2000-390321

(51) Int. Cl.
*A61K 31/445* (2006.01)
*C07D 211/68* (2006.01)
*C07D 211/80* (2006.01)
*C07D 213/02* (2006.01)

(52) U.S. Cl. ...................................... 514/318; 546/194
(58) Field of Classification Search ................ 546/194; 514/318

See application file for complete search history.

(56) References Cited

U.S. PATENT DOCUMENTS

| | | | |
|---|---|---|---|
| 5,869,501 A | 2/1999 | Hirayama et al. | ........... 514/319 |
| 6,140,351 A | 10/2000 | Arnaiz et al. | ............... 514/336 |
| 6,313,122 B1 | 11/2001 | Beight et al. | ............. 514/237.5 |
| 6,313,151 B1 | 11/2001 | Beight et al. | ................. 514/352 |
| 6,372,759 B1 | 4/2002 | Beight et al. | ................. 514/318 |
| 6,376,515 B2 | 4/2002 | Zhu et al. | .................... 514/318 |
| 6,380,221 B1 | 4/2002 | Arnaiz et al. | ............... 514/337 |
| 6,417,200 B1 | 7/2002 | Beight et al. | ................. 514/330 |
| 6,632,815 B2 | 10/2003 | Zhu et al. | ................. 514/236.5 |
| 6,642,224 B1 | 11/2003 | Hirayama et al. | ....... 514/217.04 |
| 2002/0002183 A1 | 1/2002 | Zhu et al. | |
| 2002/0091116 A1 | 7/2002 | Zhu et al. | |
| 2004/0058959 A1 | 3/2004 | Herron et al. | ............... 514/326 |
| 2004/0097491 A1 | 5/2004 | Herron et al. | ............... 514/221 |
| 2007/0021472 A1 | 1/2007 | Zhu et al. | .................... 514/352 |

FOREIGN PATENT DOCUMENTS

| | | |
|---|---|---|
| EP | 0 798 295 | 10/1997 |
| JP | 2000-302765 | 10/2000 |
| WO | WO 96/16940 | 6/1996 |
| WO | WO 99/00121 | 1/1999 |
| WO | WO 99/00126 | 1/1999 |
| WO | WO 99/00127 | 1/1999 |
| WO | WO 99/00128 | 1/1999 |
| WO | WO 99/32477 | 7/1999 |
| WO | WO 99/37643 | 7/1999 |
| WO | WO 00/39111 | 7/2000 |
| WO | WO 00/39117 | 7/2000 |
| WO | WO 00/39118 | 7/2000 |
| WO | WO 01/19788 | 3/2001 |
| WO | WO 01/19798 | 3/2001 |
| WO | WO 01/64642 | 9/2001 |
| WO | WO 01/64643 | 9/2001 |

*Primary Examiner*—Rebecca L Anderson
(74) *Attorney, Agent, or Firm*—Fitzpatrick, Cella, Harper & Scinto

(57) ABSTRACT

There are provided compounds having an anticoagulant action on the basis of inhibition of activated blood coagulation factor X and being useful as anticoagulants or preventive/therapeutic agents for diseases induced by thrombosis or embolism. Effective ingredients are the compounds such as 4'-bromo-2'-[(5-chloro-2-pyridyl)carbamoyl]-6'-β-D-galactopyranosyloxy-1-isopropylpiperidine-4-carboxanilide, 2'-(2-acetamido-2-deoxy-β-D-glucopyranosyloxy)-4'-bromo-6'-[(5-chloro-2-pyridyl)carbamoyl]-1-isopropylpiperidine-4-carboxanilide, etc. or salts thereof.

7 Claims, No Drawings

SUBSTITUTED BENZENE DERIVATIVES OR SALTS THEREOF

TECHNICAL FIELD

The present invention relates to a novel substituted benzene derivative or a salt thereof which is useful as a pharmaceutical agent particularly as an activated blood coagulation factor X inhibitor and also to such a pharmaceutical agent.

BACKGROUND OF THE INVENTION

With the changes into European and American life styles and the increase in aged population in recent years, the number of patients with thromboembolic diseases including myocardial infarction, cerebral thrombosis and peripheral arterial thrombosis have been increasing year by year and social importance of their treatment has been increasing more and more. As well as the fibrinolysis therapy and antiplatelet therapy, the anticoagulation therapy takes a part of the medical therapy in treating and preventing thrombosis (*Sogo Rinsho*, 41: 2141-2145, 1989). In particular, the safety which withstands long-term administration and accurate and proper expression of the anticoagulation activity are essential in the prevention of thrombosis. Warfarin potassium is frequently used in the world as the sole oral anticoagulant but this drug is extremely difficult to use clinically because it is difficult to control the anticoagulation capacity due to the characteristics based on its action mechanism (*J. Clinical Pharmacology*, 32, 196-209, 1992 and *N. Eng. J. Med.*, 324(26), 1865-1875, 1991) whereby a great concern has been directed toward the development of more useful and easily usable anticoagulants.

Thrombin controls conversion of fibrinogen into fibrin which is the final step of coagulation and is also concerned deeply in the activation and aggregation of platelets ("T-PA and Pro-UK" edited by S. Matsuo, published by Gakusai Kikaku, pp. 5-40 "Blood Coagulation", 1986) and its inhibitor has been the center of anticoagulant studies as a target of development of pharmaceuticals. However, thrombin inhibitors which can be administered orally have not been put into the market until now because of their low bioavailability by oral administration and problems from the viewpoint of safety (*Biomed. Biochim. Acta*, 44, 1201-1210, 1985).

Activated blood coagulation factor X is a key enzyme which is located at the joining point of the extrinsic and intrinsic coagulation cascade reactions and located upstream to thrombin whereby there is a possibility that inhibition of this factor is more efficient than the thrombin inhibition and such an inhibitor can inhibit this coagulation system in a specific manner (*THROMBOSIS RESEARCH* (19), 339-349, 1980).

As the compounds having an activated blood coagulation factor X inhibiting action, amidinonaphthyl alkylbenzene derivatives or salts thereof have been known (Japanese Patent Laid-Open No. 208946/1993; *Thrombosis Haemostasis*, 71(3), 314-319, 1994; and *Thrombosis Haemostasis*, 72(3), 393-396, 1994).

In WO 96/16940, it is mentioned that an amidinonaphthyl derivative or a salt thereof represented by the following formula is the compound having an activated blood coagulation factor X inhibiting action.

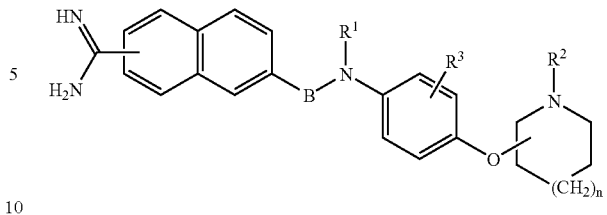

(for the symbols in the formula, refer to the gazette)

In WO 99/00121, WO 99/00126, WO 99/00127, WO 99/00128, WO 00/39111, WO 00/39117 and WO 00/39118, phenylenediamide compounds represented by the following formula, etc. are mentioned as an Xa factor inhibitor.

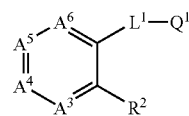

(for the symbols in the formula, refer to each of the gazettes)

Further, in WO 99/32477, a broad range of compounds represented by the following formula is mentioned as an anticoagulant.

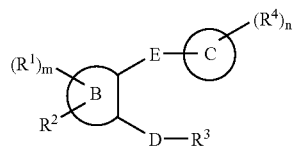

(for the symbols in the formula, refer to the gazette)

In an anticoagulation therapy, activated blood coagulation factor X inhibitor is expected to inhibit coagulation system effectively and specifically as compared with a thrombin inhibitor. Accordingly, there has been a brisk demand for creating a selective activated blood coagulation factor X inhibitor which has different chemical structure from the above-mentioned known compounds, is able to be administered per os and has further excellent effect.

DISCLOSURE OF THE INVENTION

As a result of various studies, the present inventors have found that a substituted benzene derivative represented by the following formula (I) or a salt thereof having a characteristic in terms of chemical structure where a benzene ring or a hetero ring (A ring) is bonded with a benzene ring via an amide bond ($X^1$), etc., the said benzene ring is further bonded with a piperidine ring or a benzene ring (B ring) via an amide bond ($X^2$), etc., the central benzene ring always has —$OR^4$ (—OH, —O—$SO_3H$ or —O-sugar residue) and $R^1$ has always a substituent other than hydrogen atom (halogen atom, a lower alkyl which may be substituted with halogen atom or a lower alkoxy which may be substituted with halogen atom) has an excellent activated blood coagulation factor X inhibiting action and particularly has an excellent activity per os whereupon the present invention has been achieved.

Thus, the present invention relates to a substituted benzene derivative represented by the following formula (I) or a salt thereof and also to a pharmaceutical composition having the same as an effective ingredient, particularly to an activated blood coagulation factor X inhibitor.

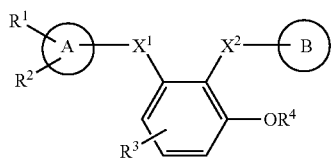

(I)

(each of the symbols in the above formula has the following meaning.

$X^1$: —C(=O)—NR$^5$—, —NR$^5$—C(=O)—, —CH$_2$—NR$^5$— or —NR$^5$-CH$_2$—;

$X^2$: —C(=O)—NR$^6$—, —NR$^6$—C(=O)—, —CH$_2$—NR$^6$— or —NR$^6$—CH$_2$—;

$R^1$: halogen atom, a lower alkyl which may be substituted with halogen atom or a lower alkoxy which may be substituted with halogen atom;

$R^2$ and $R^3$: same or different and each is hydrogen atom, halogen atom, CN, —NH—SO$_2$-(lower alkyl), —NH—CO-(lower alkyl), —CO-(lower alkyl), —CO-(lower alkoxy), —CON—H$_2$, a lower alkyl which may be substituted with halogen atom, a lower alkoxy which may be substituted with halogen atom or —S-(lower alkyl);

$R^4$: hydrogen atom, —SO$_3$H or sugar residue;

A ring: a benzene ring or a five- or six-membered hetero ring containing 1 to 4 hetero atom(s) which is/are one or more selected from a group consisting of N, S and O;

B ring: a piperidine ring in which nitrogen atom is substituted with $R^7$ when $R^4$ is hydrogen atom or —SO$_3$H or, when $R^4$ is a sugar residue, it is a piperidine ring in which nitrogen atom is substituted with $R^7$ or a benzene ring substituted with

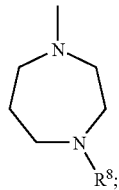

$R^5$ and $R^6$: same or different and each is hydrogen atom or a lower alkyl; and $R^7$ and $R^8$: each is hydrogen atom, lower alkyl, —SO$_2$-(lower alkyl) or a five- or six-membered hetero ring containing 1 to 4 hetero atom(s) which is/are one or more selected from a group consisting of N, S and O with a proviso that, when $X^2$ is —NR$^6$—C(=O)— and $R^4$ is hydrogen atom, the A ring means a five- or six-membered hetero ring containing 1 to 4 hetero atom(s) which is/are one or more selected from a group consisting of N, S and O.)

The compound (I) of the present invention has a different structure from Japanese laid-open patent No. 208946/1993 and WO 96/16940 in such respects that A ring is a benzene ring or a hetero ring having no amidinonaphthyl group and the $X^2$ moiety is —C(=O)—NR$^6$—, —NR$^6$—C(=O)—, —CH$_2$—NR$^6$— or —NR$^6$—CH$_2$— having no ether bond, etc.

Further, the compound (I) of the present invention has a different structure from WO 99/00121, WO 99/00126, WO 99/00127, WO 99/00128, WO 00/39111, WO 00/39117 and WO 00/39118 in such respects that $R^4$ always has hydrogen atom, —SO$_3$H or a sugar residue, the B ring has a piperidine ring in which nitrogen atom is substituted with $R^7$ or a benzene ring substituted with

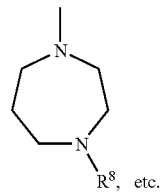

Furthermore, the compound (I) of the present invention has a different structure from the compounds specifically described in WO 99/32477 in such respects that the B ring has no thiazole ring, $R^4$ always has hydrogen atom, —SO$_3$H or a sugar residue, etc.

As hereunder, the compound (I) of the present invention will be illustrated in detail.

The term "lower" in the definition for the formula in the specification means a straight or branched carbon chain having 1-6 carbon(s) unless otherwise mentioned. Therefore, examples of the "lower alkyl" are methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-timethylpropyl, 1,2,2-trimethylpropyl, 1-ethyl-1-methylpropyl and 1-ethyl-2-methylpropyl. Among them, those having 1-3 carbon(s) are preferred and methyl and ethyl are particularly preferred. "Lower alkoxy" means "—O-(lower alkyl)" and, to be more specific, there may be exemplified methoxy, ethoxy, propoxy and isopropoxy although they are non-limitative. Methoxy and ethoxy are preferred.

Examples of "halogen atom" are fluorine atom, chlorine atom, bromine atom and iodine atom. Chlorine atom and bromine atom are particularly preferred.

"A lower alkyl which may be substituted with halogen atom" or "a lower alkoxy which may be substituted with halogen atom" is the above-mentioned "lower alkyl" or "lower alkoxy" and that where 1 to 6 hydrogen atom(s) thereof is/are substituted with "halogen atom(s)" and there are exemplified trifluoromethyl, difluoromethyl, fluoromethyl, chloromethyl, 2-chloroethyl, 2-bromoethyl and trifluoromethoxy, difluoromethoxy, fluoromethoxy, chloromethoxy, etc. although they are non-limitative. Fluoromethyl and fluoromethoxy are particularly preferred.

"Sugar residue" means a sugar residue of monosaccharide. There are exemplified sugar residues being remained after removal of one hydroxyl group especially at 1-position from sugar such as glucose, mannose, galactose, arabinose, xylose, ribose, N-acetylglucosamine, glucuronic acid, mannuronic acid, etc. although they are non-limitative but sugar residues where the said hydroxyl group is substituted with a lower alkoxy group or the like is included as well. Preferred one is a sugar residue from glucuronic acid.

With regard to "a five- or six-membered hetero ring containing 1 to 4 hetero atom(s) which is/are one or more selected from a group consisting of N, S and O", there are exemplified pyridine, pyrimidine, pyrazine, pyridazine, triazine, pyrrole, furan, thiophene, thiazole, imidazole, imidazoline, oxazole, isothiazole, pyrazole, isoxazole, triazole and tetrazole although they are non-limitative. The said hetero ring is not limited to an unsaturated ring but includes a saturated ring such as pyrrolidine, imidazolidine, pyrazolidine, piperidine, piperazine and morpholine. A hetero ring fused with a benzene ring such as quinoline, isoquinoline, quinoxaline and benzimidazole may be included as well. A pyridine ring is particularly preferred. When the said hetero ring is furan or thiophene and $R^1$ is 2-chloro or 2-methyl, $X^1$ is located at the position of other than 5 of furan or thiophene.

$X^1$ is —C(=O)—$NR^5$—, —$NR^5$—C(=O)—, —$CH_2$—$NR^5$— or —$NR^5$—$CH_2$— and more preferred ones are —C(=O)—$NR^5$— or —$NR^5$—C(=O)—. $X^2$ is —C(=O)—$NR^6$—, —$NR^6$—C(=O)—, —$CH_2$—$NR^6$— or —$NR^6$—$CH_2$— and more preferred ones are —$NR^6$—C(=O)— or —$NR^6$—$CH_2$—.

$R^5$ and $R^6$ are same or different and each is hydrogen atom or a lower alkyl and more preferred one is hydrogen atom. When both $R^7$ and $R^8$ are lower alkyls, they are particularly preferably isopropyl while, when they are hetero rings, they are preferably pyridine rings.

It is preferred that the A ring is a benzene ring or a pyridine ring.

When $R^4$ is hydrogen atom or —$SO_3H$, the B ring is a piperidine ring where nitrogen atom is substituted with $R^7$, i.e.

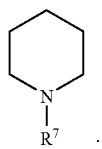

When $R^4$ is a sugar residue, the B ring is a piperidine ring where nitrogen atom is substituted with $R^7$ or a benzene ring substituted with

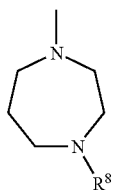

(a benzene ring substituted with a 1,4-diazepan-1-yl group where nitrogen atom is substituted with $R^8$), i.e.

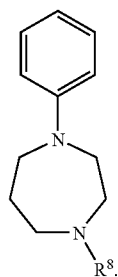

Particularly preferred compounds among the compound of the present invention are 4'-bromo-2'-[(5-chloro-2-pyridyl)carbamoyl]-6'-β-D-galactopyranosyloxy-1-isopropylpiperidine-4-carboxanilide, 2'-(2-acetamido-2-deoxy-β-D-glucopyranosyloxy)-4'-bromo-6'-[(5-chloro-2-pyridyl)carbamoyl]-1-isopropylpiperidine-4-carboxanilide, 4'-bromo-2'-[(5-chloro-2-pyridyl)carbamoyl]-6'-β-D-glucopyranosyloxy-1-isopropylpiperidine-4-carboxanilide, 5-chloro-3-[(5-chloro-2-pyridyl)carbamoyl]-2-[(1-isopropylpiperidine-4-carbonyl)amino]phenyl β-D-glucopyranoside uronic acid, 5-bromo-3-[(5-chloro-2-pyridyl)carbamoyl]-2-[(1-isopropylpiperidine-4-carbonyl)amino]phenyl β-D-glucopyranoside uronic acid, 4'-chloro-2'-[(5-chloro-2-pyridyl)carbamoyl]-6'-hydroxy-1-isopropylpiperidine-4-carboxanilide, 4'-bromo-2'-[(5-chloro-2-pyridyl)carbamoyl]-6'-hydroxy-1-isopropylpiperidine-4-carboxanilide, 2'-[(5-bromo-2-pyridyl)carbamoyl]-4'-chloro-6'-hydroxy-1-isopropylpiperidine-4-carboxanilide, 5-chloro-N-(5-chloro-2-pyridyl)-3-hydroxy-2-{[(1-isopropyl-4-piperidyl)methyl]amino}benzamide, N-(5-bromo-2-pyridyl)-5-chloro-3-hydroxy-2-{[(1-isopropyl-4-piperidyl)methyl]amino}benzamide, 3-[(4-methoxybenzoyl)amino]-2-{[(4-methyl-1,4-diazepan-1-yl)benzoyl]amino}phenyl β-D-glucopyranoside, 3-[(4-methoxybenzoyl)amino]-2-{[4-(4-methyl-1,4-diazepan-1-yl)benzoyl]amino}phenyl β-D-glucopyranoside uronic acid, etc.

The compound of the present invention includes various stereoisomers such as geometrical isomers, tautomers and optical isomers, either as mixtures or in isolated forms.

The compound of the present invention may form an acid addition salt. Further, it may form a salt with a base depending upon the type of the substituent. Specific examples of such a salt are pharmaceutically acceptable acid addition salts with an mineral acid such as hydrochloric acid, hydrobromic acid, hydroiodic acid, sulfuric acid, nitric acid and phosphoric acid or with an organic acid such as formic acid, acetic acid, propionic acid, oxalic acid, malonic acid, succinic acid, fumaric acid, maleic acid, lactic acid, malic acid, tartaric acid, citric acid, methanesulfonic acid and ethanesulfonic acid or with an acidic amino acid such as aspartic acid and glutamic acid and salts with an inorganic base such as sodium, potassium, magnesium, calcium and aluminum, an organic base such as methylamine, ethylamine and ethanolamine, a basic amino acid such as lysine and ornithine and an ammonium salt.

Further, hydrates, pharmaceutically acceptable various solvates and polymorphism of the compound of the present invention are also included in the present invention. Incidentally, it goes without saying that the present invention is not limited to the compounds mentioned in the following Examples but includes all of the substituted benzene derivatives represented by the formula (I) and pharmaceutically acceptable salts thereof.

Furthermore, the compound of the present invention includes all of the so-called prodrugs, i.e. the compounds which can be converted to the compound represented by the formula (I) or a salt thereof by metabolism in vivo. Examples of the group which forms the prodrugs of the compound of the present invention are those mentioned in *Prog. Med.* 5: 2157-2161 (1985) and those mentioned in "Iyakuhin no Kaihatsu" (Development of Pharmaceuticals) published by Hirokawa Shoten in 1990, Vol. 7, "Molecular Design", pages 163-198. Especially as the prodrug of the compound of the present invention, there will be a prodrug where a prodrug having a hydroxyl group is metabolized in vivo to give a glycoside represented by the formula (I) and such a prodrug is also included in the present invention.

Still further, the present invention of course includes a glycoside represented by the formula (I) which is produced by being subjected to metabolism in vivo.

(Production Methods)

Typical production methods of the compound of the present invention will be illustrated as hereunder.

In the case of the compound of the present invention (I) where $R^4$ is hydrogen atom, it may be prepared by the following method.

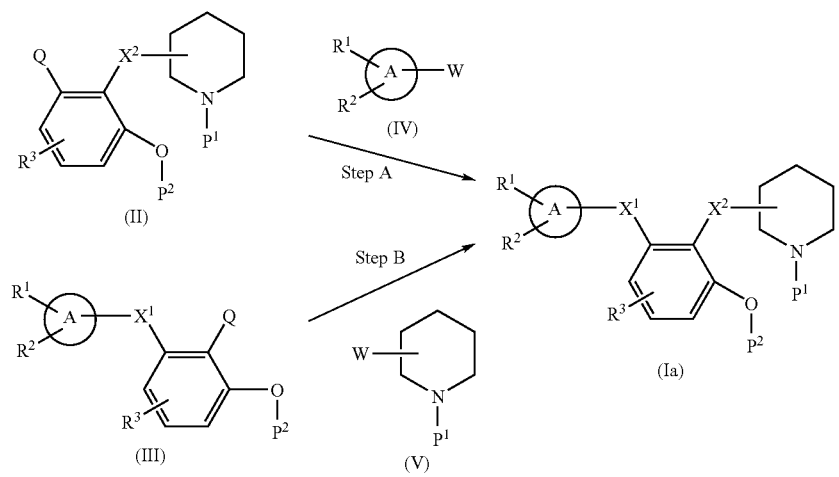

(In the formulae, A ring, $X^1$, $X^2$, $R^1$, $R^2$ and $R^3$ have the above-mentioned meanings; Q and W are that, when Q is —$NH_2$ or —NH-(lower alkyl), W means —COOH, —CHO or —$CH_2$— leaving group while, when Q is —COOH, —CHO or —$CH_2$— leaving group, W means —$NH_2$ or —NH-(lower alkyl); $P^1$ means hydrogen atom, lower alkyl or a protective group for amine; $P^2$ means hydrogen atom or a protective group for phenol; and examples of the leaving group are halogen atom, —O—$SO_2$alkyl and —O—$SO_2$-aryl.)

Step A

This is a reaction where condensation of a carboxylic acid with an amine, an aldehyde with an amine or a compound having a —$CH_2$-leaving group with an amine comprising a combination of the compound (II) with the compound (IV) is carried out to synthesize a compound (Ia).

In the case of a combination of a carboxylic acid with an amine, the present reaction is preferably in accordance with the conventional acylation reaction in the presence of a condensing agent to form an amide bond.

Examples of the condensing agent which is used advantageously are N,N-dicyclohexylcarbodiimide (DCC), 1-ethyl-3-[3-(N,N-dimethylamino)propyl]carbodiimide, carbonyldiimidazole, diphenylphosphoryl azide (DPPA) and diethylphosphoryl cyanide.

It is also possible that a carboxylic acid is made into the active derivatives of the corresponding carboxylic acid and then condensed with an amine.

Examples of the active derivative of the carboxylic acid are active ester prepared by the reaction with a compound of a phenol type such as p-nitrophenol or an N-hydroxyamine type such as 1-hydroxysuccinimide and 1-hydroxybenzotriazole, carbonic acid monoalkyl ester, mixed acid anhydride prepared by the reaction with organic acid and a phosphoric acid type mixed acid anhydride prepared by the reaction with diphenylphosphoryl chloride and N-methylmorpholine; acid azide prepared by the reaction of an ester with hydrazine and alkyl nitrite; acid halides such as acid chloride and acid bromide; and acid anhydride of a symmetric type. Usually, the above reaction is carried out in a solvent from with cooling to or at room temperature although, in some cases, it is to be carried out under an anhydrous condition depending upon the type of the acylation reaction.

Examples of the applicable solvent are inert solvents which do not participate in the reaction such as dimethylformamide, dioxane, tetrahydrofuran, ether, dichloroethane, dichloromethane, chloroform, carbon tetrachloride, dimethoxymethane, dimethoxyethane, ethyl acetate, benzene, acetonitrile, dimethyl sulfoxide, ethanol, methanol and water and a mixed solvent thereof and an appropriate selection depending upon the applied method is preferred.

In addition, depending upon the applied method, there are some cases where the reaction smoothly proceeds in the presence of a base or using such a base as a solvent where the base is N-methylmorpholine, triethylamine, trimethylamine, pyridine, sodium hydride, potassium tert-butoxide, butyl lithium, sodium amide, potassium carbonate, sodium carbonate, sodium hydrogen carbonate, cesium carbonate or the like.

Any of the reactions besides the above-mentioned ones may be used so far as the reaction forms an amide bond.

In the case of the combination of the aldehyde and the amine, the reaction may be carried out according to a usual reductive amination reaction in the presence of a reducing agent.

As the reducing agent, sodium borohydride, sodium cyanoborohydride, sodium triacetoxyborohydride, borane-trimethylamine complex and the like can be suitably used. Further, catalytic hydrogenation may be carried out at atmospheric pressure or under an elevated pressure in the presence of a catalyst such as palladium-carbon and platinum oxide. The reaction is carried out under cooling or heating in alcohol or in a solvent that does not participate in the reaction. In addition, depending upon the applied method, there are some cases where the reaction smoothly proceeds in the presence of an acid such as acetic acid, toluenesulfonic acid and sulfuric acid or using such an acid as a solvent.

In the case of the combination of the $CH_2$-leaving group-containing compound and the amine, the reaction may be carried out according to a usual N-alkylation reaction.

The reaction is carried out under cooling or heating in a solvent that does not participate in the reaction. In addition, depending upon the applied method, there are some cases where the reaction smoothly proceeds in the presence of the base as described above or using such a base as a solvent.

Step B

This is a reaction where reaction of a carboxylic acid with an amine, an aldehyde with an amine or a compound having a —$CH_2$-leaving group with an amine comprising a combination of the compound (III) and the compound (V) is carried out to synthesize a compound (Ia). This reaction is carried out by the same manner as in the step A.

When $P^1$ in the compound (Ia) of the present invention is a protective group for amine and the protective group is not cleaved during the steps A and B, a cleavage using a method suitable for cleaving the protective group $P^1$, for example, cleavage by acid such as trifluoroacetic or cleavage by reduction adding catalytic hydrogen, is carried out whereupon it is possible to give a compound of the present invention (I) in which $R^1$ is hydrogen atom. Further, when $P^2$ of the compound (Ia) of the present invention is a protective group for phenol and the protective group is not cleaved during the steps A and B, cleavage using a method suitable for cleaving the protective group $P^2$ such as cleavage by reduction adding catalytic hydrogen, cleavage by pentamethylbenzene and trifluoroacetic acid or cleavage by hydrolysis using a base such as sodium hydroxide is carried out whereupon it is possible to give a compound of the present invention (I) where $R^4$ is hydrogen atom.

With regard to the protective group for amine exemplified for $P^1$, there is no particular limitation so far as it is a group which is usually used for protection of amine and its examples are lower alkoxycarbonyl, aralkyloxycarbonyl, acyl, lower alkyl, aralkyl and sulfonyl or the like.

With regard to the protective group for phenol exemplified for $P^2$, there is no particular limitation so far as it is a group which is usually used for protection of phenol and its examples are optionally substituted lower alkyl, aralkyl, tri(lower alkyl)silyl, lower alkylcarbonyl, lower alkyloxycarbonyl and sulfonyl. "Aralkyl" means a group where hydrogen atom of the above alkyl is substituted with aryl and its specific examples are benzyl and phenylethyl. Specific examples of "acyl" are formyl, acetyl, propionyl and butyryl.

Further, a method which is shown by the following reaction formulae is exemplified as a particularly effective method.

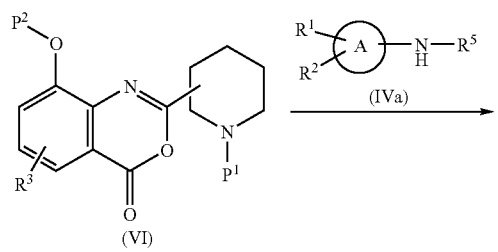

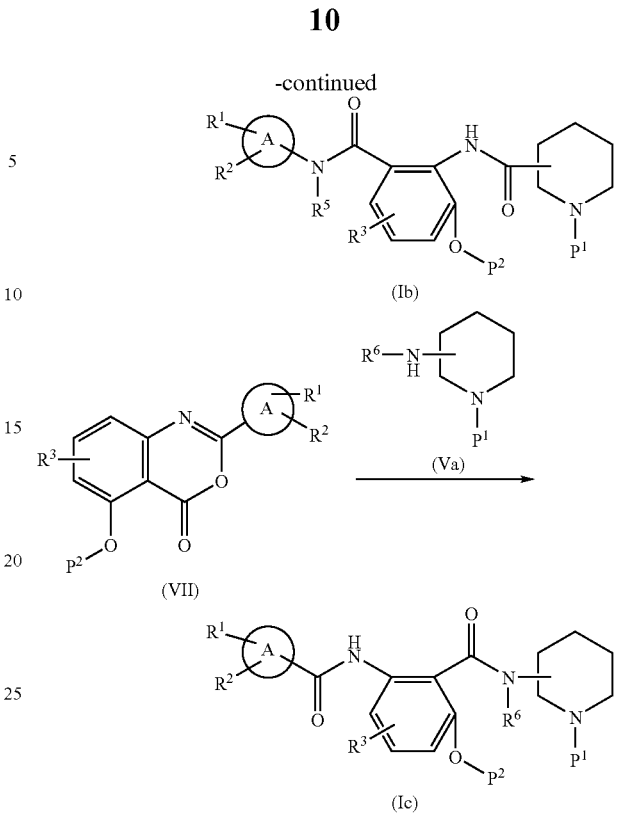

(In the formulae, A ring, $P^1$, $P^2$, $R^1$, $R^2$, $R^3$, $R^5$ and $R^6$ have the above-mentioned meanings.)

This is a reaction where an amide linkage is produced by the reaction of the compound (VI) with an amine (IVa) or the compound (VII) with an amine (Va) to give a compound (Ib) or a compound (Ic) and it is carried out in the above-mentioned solvent which does not participate in the reaction from at room temperature to with heating. In addition, depending upon the applied method, there are some cases where the reaction smoothly proceeds in the presence of a base or using such a base as a solvent in which the base is N-methylmorpholine, triethylamine, trimethylamine, pyridine, sodium hydride, potassium tert-butoxide, butyl lithium, sodium amide or the like.

When the compound of the present invention (I) where $R^4$ is hydrogen atom is used and made into a sulfonic acid using a trimethylamine-sulfur trioxide complex or the like, it is possible to prepare a compound of the present invention (I) where $R^4$ is —$SO_3H$.

The compound of the present invention (I) where $R^4$ is a sugar residue may be prepared by the following method using a compound where $R^4$ is hydrogen atom or a compound which can be synthesized by a known method described in the patent gazettes cited in "Background of the Invention".

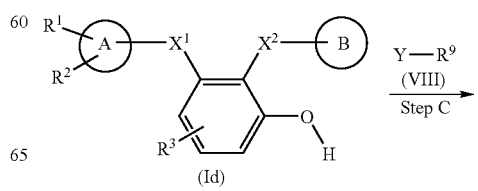

-continued

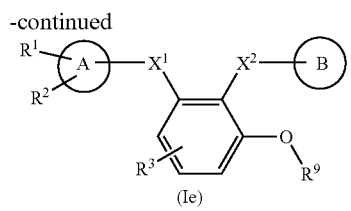

(Ie)

(In the formulae, A ring, B ring, $R^1$, $R^2$, $R^3$, $X^1$ and $X^2$ have the above-mentioned meanings; Y means a leaving group; and $R^9$ means a sugar residue which may be protected.)

Step C

This is a reaction where a sugar donor and a phenol comprising a combination of the compound (Id) and the compound (VIII) are made to react preferably in the presence of an activator to synthesize a compound (Ie) having a sugar residue which may have a protective group. This reaction may follow the common methods for the production of glycosides. Representative methods are those described in *Yuki Gosei Kagaku Kyokai Shi*, vol. 50, no. 5 (1992), pages 378~390 and in "Jikken Kagaku Koza", vol. 26, 'Yuki Gosei' VIII, pages 267~354, published in 1992 by Maruzen.

Examples of the sugar donor are sugar derivatives having a leaving group at the 1-position of the sugar. Examples of the leaving group are halogen, thioalkyl, thioheteroaryl, acyloxy, trichloroacetimidate, diaryl phosphate, diaryl phosphine imidate, tetramethylphosphoroamidate and dialkyl phosphate.

Examples of the condensing agent used are silver carbonate, silver trifluoromethanesulfonate, silver perchlorate, silver oxide, sodium hydroxide, potassium carbonate, sodium methoxide, sodium hydride, diazabicycloundecene, trimethylsilyl triflate, boron trifluoride, methyl triflate, silicon tetrafluoride, tin chloride, p-toluenesulfonic acid and salt thereof, trifluoromethanesulfonic acid anhydride, copper bromide, mercury bromide and N-bromosuccinimide.

It is also possible to use a sugar donor having, for example, a hydroxyl group at 1-position where an activator such as triphenyl phosphine, diethyl azodicarboxylate, etc. is used.

Usually, the above reaction is carried out under from cooling to heating in a solvent. Depending upon the type of the reaction for the production of glycoside, there are some cases where the reaction is to be carried out under an anhydrous condition.

With regard to a solvent, there may be used an inert solvent which does not participate in the reaction such as dimethylformamide, dioxane, tetrahydrofuran, ether, dichloroethane, dichloromethane, chloroform, carbon tetrachloride, dimethoxymethane, dimethoxyethane, ethyl acetate, benzene, toluene, acetonitrile, dimethyl sulfoxide, methanol, ethanol, etc. or a mixed solvent thereof and it is preferred to appropriately select depending upon the method applied.

Further, any reaction besides the reactions mentioned here may be used so far as it is a reaction which forms a glycoside bond.

When $R^9$ is a sugar residue which may have a protective group in the compound of the present invention (Ie) and when the said protective group is not cleaved in the step C, it is also possible to prepare the compound of the present invention where $R^9$ is a sugar residue having no protective group by means of cleavage using a method which is appropriate for cleaving the said protective group such as cleavage by hydrolysis using a base such as sodium carbonate or cleavage by reduction such as addition of catalytic reduction.

There is no particular limitation for the protective group so far as it is a group which is usually used for protection of hydroxyl group, carboxyl group, etc. and its examples are optionally substituted lower alkyl, aralyl, tri(lower alkyl)silyl and acyl. "Aralkyl" means a group where hydrogen atom of the above-mentioned lower alkyl is substituted with aryl and its specific examples are benzyl, etc. Specific examples of "acyl" are acetyl, propionyl, isopropionyl and benzoyl.

Incidentally, the material compounds for the compounds of the present invention may be produced by the following representative method.

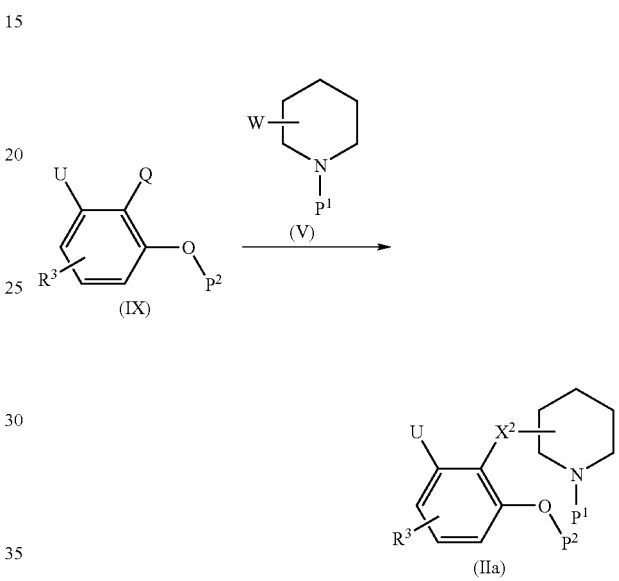

(In the formula, $R^3$, $X^2$, $P^1$, $P^2$, Q and W have the same meanings as mentioned already; U is —COOH, —COOP$^3$, —NH$_2$, —NH-(lower alkyl), —NH—P$^4$, —N(P$^4$)-(lower alkyl), NO$_2$, —CHO, —CH$_2$OH, -(lower alkyl) or a —CH$_2$-leaving group; and P$^3$ and P$^4$ are protective groups for carboxyl and amine, respectively)

This is a reaction where condensation of a carboxylic acid with an amine, an aldehyde with an amine or a compound having a —CH$_2$-leaving group with an amine comprising a combination of the compound (IX) with the compound (V) is carried out to synthesize a compound (IIa). This reaction is carried out by the same manner as in the above-mentioned step A. When U means NO$_2$ in the compound (IIa), a compound where U is —NH$_2$ can be produced by conducting a reduction reaction; when U means —COOH or —COOP$^3$, a compound where U is —CHO can be produced by conducting a reduction reaction; when U means —CH$_2$OH or -(lower alkyl), a compound where U is —CHO or —COOH can be produced by conducting an oxidation reaction; and when U means —COOP$^3$, —NH—P$^4$ or —N(P$^4$)-(lower alkyl), a compound where U is —COOH, —NH$_2$ or —NH-(lower alkyl) can be produced by means of a method suitable for cleaving each of the protective groups such as, for example, cleavage by hydrolysis using a base such as sodium hydroxide or an acid such as hydrochloride acid, cleavage by reduction such as addition of catalytic hydrogen or cleavage using an acid such trifluoroacetic acid.

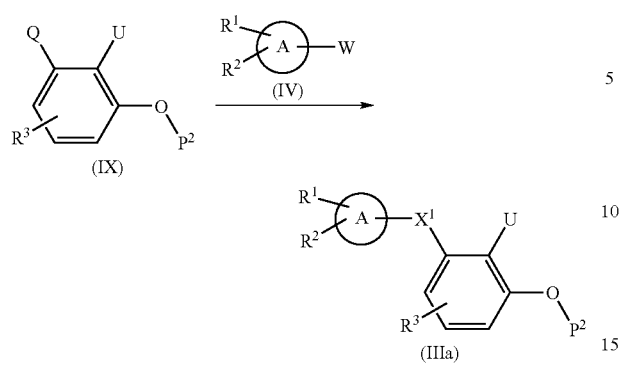

(In the formula, A ring, $R^1$, $R^2$, $R^3$, $X^1$, $P^2$, Q, W and U have the above-mentioned meanings)

This is a reaction where condensation of a carboxylic acid with an amine, an aldehyde with an amine or a compound having a —CH$_2$-leaving group with an amine comprising a combination of the compound (IX) with the compound (IV) is carried out to synthesize a compound (IIIa). This reaction is carried out by the same manner as in the above-mentioned step A. When U means NO$_2$ in the compound (IIIa), a compound where U is —NH$_2$ can be produced by conducting a reduction reaction; when U means —COOH or —COOP$^3$, a compound where U is —CHO can be produced by conducting a reduction reaction; when U means —CH$_2$OH or -(lower alkyl), a compound where U is —CHO or —COOH can be produced by conducting an oxidation reaction; and when U means —COOP$^3$, —NH—P$^4$ or —N(P$^4$)-(lower alkyl), a compound where U is —COOH, —NH$_2$ or —NH-(lower alkyl) can be produced by means of a method suitable for cleaving each of the protective groups such as, for example, cleavage by hydrolysis using a base such as sodium hydroxide or an acid such as hydrochloride acid, cleavage by reduction such as addition of catalytic hydrogen or cleavage using an acid such trifluoroacetic acid.

The method as shown by the following reaction formulae is particularly effective for the synthesis of the compounds represented by the formulae (II) and (III).

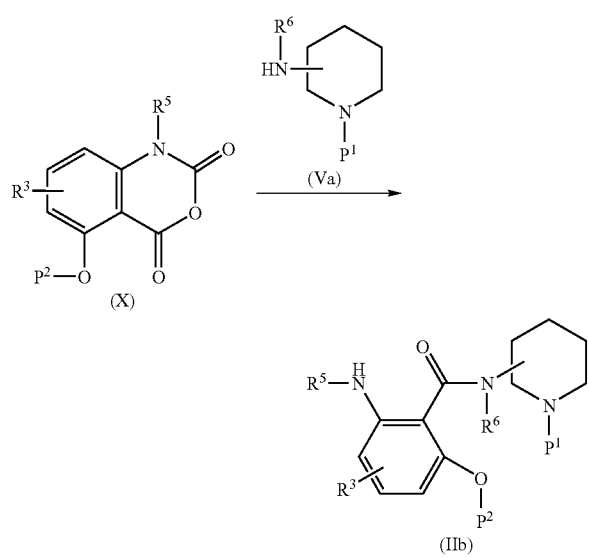

(In the formulae, A ring, $R^1$, $R^2$, $R^3$, $R^5$, $R^6$, $P^1$ and $P^2$ have the above-mentioned meanings)

This is a reaction where an amide bond is formed by the reaction of the compound (X) with an amine (Va) or the compound (XI) with an amine (IVa) whereupon the compound (IIb) or the compound (IIIa) is prepared and the reaction is carried out from at room temperature to with heating in the above-mentioned inert solvent. Depending upon the method applied thereto, there may be the case where the reaction proceeds smoothly when the reaction is carried out in the presence of a base such as N-methylmorpholine, triethylamine, trimethylamine, pyridine, sodium hydride, potassium tert-butoxide, butyl lithium or sodium amide or using such a base as a solvent.

Incidentally, the step for the introduction of sugar residue is not limited to the above-mentioned steps only. Thus, it is possible to manufacture the compound by an optional combination of the steps which can be usually adopted by persons skilled in the art such as a step that a sugar donor and a phenol comprising a combination of the compound (VIII) with the compound (II), (III), (VI), (VII), (IX), (X) or (XI) are made to react preferably in the presence of an activator whereupon the compound having a sugar residue which may be protected is synthesized and then it is condensed with (IV), (IVa), (V) or (Va) according to the method descirbed above.

Further, the compound represented by the formula (I) can be manufactured by an optional combination of the known steps which are able to be adopted by persons skilled in the art such as alkylation, acylation, oxidation, reduction and hydrolysis.

The compound of the present invention which is produced as such can be isolated and purified by known techniques such as extraction, precipitation, separation chromatography, fractionating crystallization, recrystallization, etc. Also, the compound of the present invention can be made into desired salts by subjecting it to a usual salt forming reaction.

In addition, the compound of the present invention may exist in the form of optical isomers when it has asymmetric carbon atoms. Those optical isomers can be separated in the usual method by a fractionating crystallization in which an isomer is recrystallized together with an appropriate salt or by a column chromatography or the like.

INDUSTRIAL APPLICABILITY

The compound of the present invention shows a potent anticoagulation action by inhibiting the activated blood coagulation factor X in a specific manner. Accordingly, the compound is useful as a blood coagulation inhibitor or a drug for use in the prevention and the treatment of diseases which are induced by thrombus or embolus.

Examples of such diseases applicable include cerebrovascular disorders such as cerebral infarction, cerebral thrombosis, cerebral embolism, transient cerebral ischemic attack (TIA), subarachnoid hemorrhage (vascular twitching) and the like, ischemic heart diseases such as acute or chronic myocardial infarction, unstable angina, coronary artery thrombolysis and the like, pulmonary vascular disorders such as pulmonary thrombosis, pulmonary embolism and the like, and various vascular disorders such as peripheral arterial obstruction, deep venous thrombosis, disseminated intravascular coagulation syndrome, thrombus formation after artificial blood vessel operation or after artificial valve replacement, re-occlusion and re-stricture after coronary artery by-pass operation, re-occlusion and re-stricture after PTCA (percutaneous transluminal coronary angioplasty) or PTCR (percutaneous transluminal coronary re-canalization) operation and thrombus formation at the time of extracorporeal circulation.

In addition, a possibility has been suggested on the use of the compound of the present invention as a drug for use in the prevention and the treatment of influenza virus infection based on the activity to inhibit the growth of influenza virus, effected by the activated blood coagulation factor X inhibiting action of the compound of the present invention (Japanese Patent Laid-Open No. 227971/1994).

Of the compound of the present, the excellent activity invention to inhibit the activated blood coagulation factor X and the excellent action to extend the coagulation time by oral administration have been confirmed by the following tests.

1) An In Vitro Test on Measurement of Coagulation Time by Human Activated Blood Coagulation Factor X To 90 µl of human blood plasma were added 10 µl of a drug or a physiological saline and 50 µl of human factor Xa (Enzyme Research Labs), incubation was carried out at 30° C. for 3 minutes, 100 µl of 20 mM $CaCl_2$ previously warmed at 37° C. were added and the time until coagulation was measured by a coagulo-meter (KC10 of Amelung). With regard to the human blood plasma, each 45 ml of blood were collected from vein of elbow of six healthy persons using a syringe in which 5 ml of 3.8% sodium citrate were contained and centrifuged at 4° C. for 15 minutes at 3,000 rpm and the separate blood plasma was pooled and frozen, then thawed before use. With regard to the human factor Xa, the concentration by which the coagulation time when a physiological saline solution (control) was added was about 30 to 40 seconds was selected. A $CT_2$ value (concentration by which the coagulation time is prolonged to an extent of 2-fold) was determined by plotting the drug concentrations and relative value (fold) of the coagulation time to the control, followed by subjecting to linear regression. The results are shown in the following Table 1.

TABLE 1

| Compound | Test on Measurement of Coagulation Time by Human Activated Blood Coagulation Factor X ($CT_2$) (µM) |
|---|---|
| Example 1 | 0.295 |
| Example 3 | 0.062 |
| Example 8 | 0.137 |
| Example 10 | 0.617 |
| Example 18 | 0.153 |

2) An In Vitro Test on Measurement of Coagulation Time by Bovine Thrombin

To 50 µl of human blood plasma was added 50 µl of a drug or a physiological saline, incubation was carried out at 37° C. for 3 minutes, 50 µl of thrombin (500 units of Thrombin (derived from bovine; Mochida Pharmaceutical)) previously warmed at 37° C. was added and the time until coagulation was measured by a coagulo-meter (KC10 of Amelung). With regard to the human blood plasma, each 45 ml of blood was collected from vein of elbow of six healthy persons using a syringe in which 5 ml of 3.8% sodium citrate was contained and centrifuged at 4° C. for 15 minutes at 3,000 rpm and the separated blood plasma was pooled and frozen, the concentration by which the coagulation time when a physiological saline (control) was added was about 20 second was selected. A $CT_2$ value (concentration by which the coagulation time is prolonged to an extent of 2-fold) was determined by plotting the drug concentrations and relative value (fold) of the coagulation time to the control, followed by subjecting to linear regression.

As a result, all $CT_2$ values for the compounds of Examples 10 and 18 were not lower than 100 µM.

3) Test on Measurement of Enzyme Inhibition by Synthetic Substrate Method

To a 96-well microplate were added 80 µl of a reaction buffer (pH 8.4), 15 µl of a compound solution and 30 µl of 2 mM synthetic substrate S-2222 (Chromogenix), then 25 µl of 0.025 U/ml of human activated blood coagulation factor X (Factor Xa; Enzyme Research Labs) was added, the reaction was carried out at 37° C. for 10 minutes, changes in absorbance 405 nm were measured by a Bio-Rad Model 3550 and $IC_{50}$ was calculated.

As a result of measurements of the above 1), 2) and 3), it was confirmed that the compound of the present invention inhibits human activated blood coagulation factor X in a specific manner and shows a potent anticoagulation action to blood. It was confirmed that the compounds shown in Examples 1, 3, 8, 10 and 18 of the present invention extend the coagulation time at low concentration showing an excellent anti-blood coagulation action.

4) Test on Ex Vivo Measurement of Coagulation Time in Cynomolgus Monkeys (Oral Administration)

A drug (5 mg/ml or 0.5 mg/ml) which was dissolved (suspended) in 0.5% methylcellulose was compulsorily administered per os at a dose of 2 ml/kg (10 mg/kg or 1 mg/kg) via an oral gavage after blood collection before the administration of the drug to a male cynomolgus monkeys (body weight around 4 kg) fasted for 12 hours or longer and, after 1, 2, 4, 6 and 8 hour(s), 2 ml of blood was collected from femoral vein using 1/10 volume of 3.8% sodium citrate and blood plasma was separated by means of centrifugal treatment of 3,000 rpm for 10 minutes. Using the resulting blood plasma, extrinsic coagulation time (PT) and intrinsic coagulation time (APTT) were measured in accordance with the following methods a) and b). The experiment was carried out under non-anesthetization. Incidentally, the values are shown in terms of the relative ratio of the coagulation time of the drug-administered group to the coagulation time of the control (no drug administered) group and the value of the blood collection point showing the most potent extending action for the coagulation time is described there.

a) Extrinsic Coagulation Time (PT)

Ortho Brain Thromboplastin (54 mg/vial; a freeze-dried preparation; Ortho-Clinical Diagnostics) was dissolved in 2.5 ml of Milli-Q water and preliminarily warmed at 37° C. The above-separated blood plasma (50 µl) was warmed at 37° C. for 1 minute, 50 µl of the above-mentioned thromboplastin solution was added and the coagulation time was measured. KC10 of Amelung was used for the measurement of the coagulation time. The result is shown in the following Table 2.

TABLE 2

| Compound | Dose | Test on Measurement of Coagulation Time in Cynomolgus Monkeys (PT) |
|---|---|---|
| Example 1 | 10 mg/kg | 7.69 |
| Example 3 | 10 mg/kg | 5.60 |
| Example 18 | 1 mg/kg | 1.94 |
| Example 19 | 1 mg/kg | 2.26 |
| Control Compound | 10 mg/kg | 2.00 |

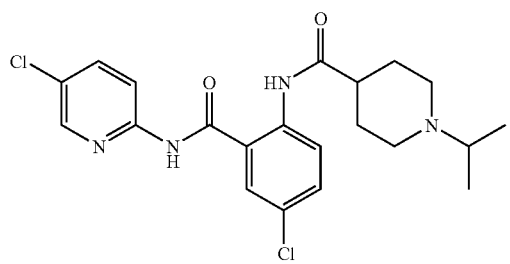

(Control)

(Example 44 of WO 00/39118)

As a result of this test, the compounds of the present invention were found to have an excellent action of extending the coagulation time even by oral administration. As compared with Example 44 (control) of WO 00/39118, the compounds of Examples 1 and 3 of the present invention were confirmed to have longer extending action for the coagulation time by the same dose and to show an excellent anticoagulation action. In addition, the compounds shown in Examples 18 and 19 showed the similar action for extending the coagulation time by the dose of one-tenth as compared with the control and were confirmed to show an excellent anticoagulation action.

b) Intrinsic Coagulation Time (APTT)

To 50 μl of the above blood plasma were added 50 μl of Hemoliance Thrombosil I (Dia-Iatron), the mixture was warmed at 37° C. for 3 minutes, 50 μl of a 20 mM $CaCl_2$ solution previously warmed at 37° C. were added and the coagulation time was measured. KC10A manufactured by Amelung was used for the measurement of the coagulation time.

Dose dependency of and time-course changes in the anticoagulation action were also examined by changing the administration dose or the blood collection time.

The pharmaceutical composition which contains one or more compound(s) of the present invention represented by the formula (I) or pharmaceutically acceptable salts thereof as the active ingredient is prepared into tablets, diluted powders, fine granules, granules, capsules, pills, solutions, injections, suppositories, ointments, plasters and the like using commonly used pharmaceutical carriers, fillers and other additives and administered either orally or parenterally (such as injection, percutaneous, permucous, etc.).

Clinical dose of the compound of the present invention in human is optionally decided by taking symptoms, body weight, age, sex and the like of each patient to be treated into consideration and, usually, it is 0.1 to 500 mg by oral administration or 0.01 to 100 mg by parenteral administration per day per adult where the daily dose is divided into one to several time(s) per day. Since the dose varies under various conditions, a smaller dose than the above range may be sufficient in some cases.

The solid composition for use in the oral administration according to the present invention is used in the form of tablets, diluted powders, granules and the like. In such a solid composition, one or more active substance(s) is/are mixed with at least one inert diluent such as lactose, mannitol, glucose, hydroxypropyl cellulose, microcrystalline cellulose, starch, polyvinylpyrrolidone, metasilicic acid or magnesium aluminate. In the usual manner, the composition may contain additives other than the inert diluent, such as a lubricant (e.g., magnesium stearate), a disintegrating agent (e.g., calcium cellulose glycolate), a stabilizing agent (e.g., lactose) and a solubilizing agent or a solubilizing aid (e.g., glutamic acid and aspartic acid). If necessary, tablets or pills may be coated with a film of a gastric or enteric substance such as sucrose, gelatin, hydroxypropyl cellulose, hydroxypropyl methylcellulose phthalate or the like.

The liquid composition for oral administration includes pharmaceutically acceptable emulsions, solutions, suspensions, syrups, elixirs and the like and contains a commonly used inert diluent such as pure water or ethyl alcohol. In addition to the inert diluent, this composition may also contain auxiliary agents such as a solubilizing agent or a solubilizing aid, a moistening agent, a suspending agent and the like, as well as sweeteners, flavors, aromas and antiseptics.

The injections for parenteral administration include aseptic aqueous or non-aqueous solutions, suspensions and emulsions. Examples of the diluent for use in the aqueous solutions and suspensions include distilled water for injection use and physiological saline. Examples of the diluent for use in the non-aqueous solutions and suspensions include propylene glycol, polyethylene glycol, a vegetable oil (e.g., olive oil), an alcohol (e.g., ethyl alcohol), Polysorbate 80 (trade name) and the like.

Such a composition may further contain additive agents such as isotonic agent, an antiseptic agent, a moistening agent, an emulsifying agent, a dispersing agent, a stabilizing agent (e.g., lactose) and a solubilizing agent or a solubilizing aid. Those compositions are sterilized by filtering through a bacteria retaining filter, blending of a germicide or irradiation. Alternatively, they may be used by firstly making into sterile solid compositions and dissolving them in sterile water or a sterile solvent for injection prior to their use.

When the compound of the present invention has a low solubility, it may be subjected to a solubilization treatment. The solubilization treatment may be carried out by known methods which can be applied to pharmaceutical preparations such as a method in which surface-active agents (polyoxyethylene hydrogenated castor oil, polyoxyethylene sorbitan higher fatty acid esters, polyoxyethylene polyoxypropylene glycols, sucrose fatty acid esters and the like) are added and a method in which a drug is formed into a solid dispersion together with a solubilizing agent such as a polymer (e.g., a water soluble high polymer such as hydroxypropyl methylcellulose (HPMC), polyvinylpyrrolidone (PVP) and polyethylene glycol (PEG) or an enteric polymer such as carboxymethyl ethylcellulose (CMEC), hydroxypropyl methylcellulose phthalate (HPMCP) and methyl methacrylate-methacrylic acid copolymer (Eudragit L and S, trade names, manufactured by Rohm & Haas). In addition, as occasion demands, a method in which a drug is made into a soluble salt or a method in which an inclusion compound is formed using cyclodextrin or the like may be employed. The solubilizing means may be appropriately changed depending upon each drug of interest [Saikin no Seizai Gijutsu to Sono Oyo (Recent Pharmaceutical Technology and Application), I. Utsumi, et al., *Iyaku Journal,* 157-159 (1983) and Yakugaku Monograph, No. 1, Bioavailability, K. Nagai, et al., published by Soft Science, 78-82 (1988)]. Among the above techniques, a method in which solubility of a drug is improved by forming its solid dispersion with a solubilizing agent may be preferably employed (Japanese Patent Laid-Open No. 49314/1981 and FR 2460667).

BEST MODE FOR CARRYING OUT THE INVENTION

The following description specifically illustrates the production method of the compounds of the present invention with reference to the production examples of the compounds of the present invention. In this connection, since novel compounds are included in the starting material compounds for the compounds of the present invention, production methods of them are also described as reference examples.

REFERENCE EXAMPLE 1

Lithium aluminum hydride (500 mg) was suspended in 40 ml of tetrahydrofuran, a solution of 3.55 g of ethyl 1-isopropylpiperidine-4-carboxylate in 10 ml of tetrahydrofuran was added thereto at −50° C. and the mixture was stirred for 2.5 hours from under ice-cooling to at room temperature. To this were added 0.5 ml of water, 0.5 ml of a 2N aqueous solution of sodium hydroxide, 1.5 ml of water and anhydrous magnesium sulfate under ice-cooling, the resulting precipitate was removed by filtration and the solvent was evaporated in vacuo to give 2.96 g of (1-isopropyl-4-piperidyl)methanol.

REFERENCE EXAMPLE 2

Oxalyl chloride (3.15 ml) was dissolved in 30 ml of dichloromethane, a solution of 3.20 ml of dimethyl sulfoxide in 6 ml of dichloromethane was added thereto at −70° C., the mixture was stirred for 15 minutes, a solution of 2.93 g of (1-isopropyl-4-piperidyl)methanol in 15 ml of dichloromethane was added thereto at −70° C. and the mixture was stirred for 1 hour. After 12.5 ml of triethylamine were added at −70° C., the mixture was raised to room temperature, then water and a saturated aqueous solution of sodium hydrogen carbonate were added and the mixture was extracted with chloroform. The organic layer was dried over anhydrous magnesium sulfate, the solvent was evaporated in vacuo and ethyl acetate was added to the resulting residue. After removing the insoluble matter by filtration, the solvent was evaporated in vacuo to give 1.15 g of 1-isopropylpiperidine-4-carbaldehyde. This compound was used for the next reaction without purification.

REFERENCE EXAMPLE 3

3-Hydroxy-2-nitrobenzoic acid (10.5 g) was dissolved in 60 ml of N,N-dimethylformamide, then 15 ml of benzyl bromide and 19.0 g of potassium carbonate were added at 0° C. and the mixture was stirred at room temperature for one night. The reaction solution was filtered through Celite and the filtrate was concentrated in vacuo. Water was added to the resulting residue, the mixture was extracted with ether and the extract was washed with a saturated saline and dried over anhydrous magnesium sulfate. The solvent was evaporated in vacuo to give 20.7 g of benzyl 3-benzyloxy-2-nitrobenzoate.

REFERENCE EXAMPLE 4

To 20.7 g of benzyl 3-benzyloxy-2-nitrobenzoate were added 100 ml of ethanol and 120 ml of a 1N aqueous solution of sodium hydroxide and the mixture was stirred at room temperature for one night, at 60° C. for 3 hours and at 80° C. for 5 hours. After ethanol was evaporated in vacuo, the resulting aqueous solution was washed with ether and hydrochloric acid was added thereto. The resulting precipitate was collected by filtration and dried in vacuo to give 15.8 g of 3-benzyloxy-2-nitrobenzoic acid.

REFERENCE EXAMPLE 5

To 5.47 g of 3-benzyloxy-2-nitrobenzoic acid were added 20 ml of thionyl chloride and a few drops of N,N-dimethylformamide and the mixture was stirred at 80° C. for 30 minutes. The reaction solution was concentrated in vacuo, to the resulting residue were added 35 ml of pyridine and 2.55 g of 2-amino-5-chloropyridine at 0° C. and the mixture was stirred at room temperature for one night. The reaction solution was concentrated in vacuo, to the resulting residue was added a saturated aqueous solution of sodium hydrogen carbonate and the mixture was extracted with chloroform. The organic layer was dried over anhydrous magnesium sulfate, the solvent was evaporated in vacuo and an azeotropic operation was conducted with toluene to give 7.44 g of 3-benzyloxy-N-(5-chloro-2-pyridyl)-2-nitrobenzamide.

REFERENCE EXAMPLE 6

To 7.44 g of 3-benzyloxy-N-(5-chloro-2-pyridyl)-2-nitrobenzamide were added 40 ml of trifluoroacetic acid and 3.72 g of pentamethylbenzene and the mixture was stirred at 40° C. for one night. The reaction solution was concentrated in vacuo, to the residue was added a saturated aqueous solution of sodium hydrogen carbonate to such an extent that the residue did not become alkaline and the mixture was extracted with chloroform. The organic layer was extracted with 1N aqueous solution of sodium hydroxide, the aqueous layer was made acidic by addition of hydrochloric acid thereto and the mixture was extracted with chloroform. The extract was dried over anhydrous magnesium sulfate, the solvent was evaporated in vacuo and to the resulting residue were added 200 ml of suspension of Raney nickel in ethanol. This was stirred for 6 hours in a hydrogen atmosphere, N,N-dimethylformamide was added thereto and the insoluble matter was filtered off. The solvent was evaporated in vacuo and water was added to the resulting residue. The resulting precipitate was collected by filtration and dried in vacuo to give 4.58 g of 2-amino-N-(5-chloro-2-pyridyl)-3-hydroxybenzamide.

REFERENCE EXAMPLE 7

2-Amino-N-(5-chloro-2-pyridyl)-3-hydroxybenzamide (3.06 g) and 1.80 g of N-chlorosuccinimide were dissolved in 60 ml of N,N-dimethylformamide, the solution was stirred at 50° C. for 8 hours and at room temperature for 4 hours and the insoluble matter was filtered off. The solvent was evaporated in vacuo, to the resulting residue was added a 1N aqueous solution of sodium hydroxide and the mixture was extracted with ethyl acetate. The organic layer was dried over anhydrous magnesium sulfate, the solvent was evaporated in vacuo and the resulting residue was purified by means of a silica gel column chromatography. Ethanol was added to the crudely purified product and the resulting precipitate was collected by filtration and dried in vacuo to give 767 mg of 2-amino-5-chloro-N-(5-chloro-2-pyridyl)-3-hydroxybenzamide. The mother liquor was concentrated, then ethyl acetate-isopropyl ether was added thereto and the resulting precipitate was collected by filtration and dried in vacuo to give more 942 mg of the above-mentioned compound.

REFERENCE EXAMPLE 8

2-Amino-N-(5-chloro-2-pyridyl)-3-hydroxybenzamide (5.27 g) was dissolved in 60 ml of N,N-dimethylformamide and the solution was stirred at −15° C. N-Bromosuccinimide (3.56 g) was added thereto by dividing into four with an interval of 5 minutes each and the mixture was stirred at −15° C. for 1.5 hours. Then more 0.36 g of N-bromosuccinimide was added thereto, the mixture was stirred at −15° C. for 2 hours, then 120 ml of water and 120 ml of ethyl acetate were added thereto and the mixture was stirred at room temperature for 10 minutes. The resulting precipitate was filtered through Celite and an organic layer in the filtrate was collected while an aqueous layer was further extracted with ethyl acetate. Active carbon powder (2.6 g) was added to the resulting organic layer and the mixture was stirred for 15 minutes and filtered through Celite. The filtrate was washed with water and dried over anhydrous sodium sulfate, the solvent was evaporated in vacuo and the residue was dried to give 5.70 g of 2-amino-5-bromo-N-(5-chloro-2-pyridyl)-3-hydroxybenzamide.

REFERENCE EXAMPLE 9

3-Hydroxy-2-nitrobenzoic acid (2.00 g) was dissolved in 110 ml of N,N-dimethylformamide, then 1.53 g of 4-chloroaniline, 3.15 g of 1-ethyl-3-[3-(N,N-dimethylamino) propyl] carbodiimide hydrochloride and 2.21 g of 1-hydroxybenzotriazole were added thereto and the mixture was stirred at room temperature for 4 days. The reaction solution was concentrated in vacuo, a saturated saline was added to the concentrate and the mixture was extracted with chloroform. The organic layer was dried over magnesium sulfate and concentrated in vacuo. The resulting residue was purified by means of a silica gel column chromatography using chloroform: methanol (100:1) as an eluate to give 2.97 g of 4'-chloro-3-hydroxy-2-nitrobenzanilide.

REFERENCE EXAMPLE 10

To 7.09 g of 3-benzyloxy-2-nitrobenzoic acid were added 30 ml of thionyl chloride and a few drops of N,N-dimethylformamide and the mixture was stirred at 80° C. for 30 minutes. The reaction solution was concentrated in vacuo, then 40 ml of pyridine and 4.91 g of 2-amino-5-bromopyridine were added to the resulting residue at 0° C. and the mixture was stirred at room temperature for one night. The reaction solution was concentrated in vacuo, then a saturated aqueous solution of sodium hydrogen carbonate and methanol were added to the resulting residue and the mixture was extracted with chloroform. The organic layer was dried over anhydrous magnesium sulfate, the solvent was evaporated in vacuo and the residue was subjected to an azeotropic treatment with toluene to give 11.01 g of 3-benzyloxy-N-(5-bromo-2-pyridyl)-2-nitrobenzamide.

REFERENCE EXAMPLE 11

To 10.7 g of 3-benzyloxy-N-(5-bromo-2-pyridyl)-2-nitrobenzamide were added 50 ml of trifluoroacetic acid and 4.88 g of pentamethylbenzene and the mixture was stirred at room temperature for 4 days. The reaction solution was concentrated in vacuo, to the residue was added a saturated aqueous solution of sodium hydrogen carbonate to such an extent that the residue did not become alkaline and the mixture was extracted with chloroform. The organic layer was extracted with 1N aqueous solution of sodium hydroxide and concentrated hydrochloric acid was added to an aqueous layer. The resulting precipitate was collected by filtration and dried in vacuo to give 7.86 g of N-(5-bromo-2-pyridyl)-3-hydroxy-2-nitrobenzamide.

REFERENCE EXAMPLE 12

N-(5-Bromo-2-pyridyl)-3-hydroxy-2-nitrobenzamide (7.71 g) was suspended in 50 ml of ethanol and 22 ml of distilled water, then 12.7 g of reduced iron and 2.45 g of ammonium chloride were added thereto and the mixture was heated to reflux for 6 hours. After it was cooled down to room temperature, insoluble matter was filtered and washed with chloroform. The filtrate was concentrated in vacuo, a saturated aqueous solution of sodium hydrogen carbonate was added thereto, the mixture was extracted with chloroform and the extract was washed with a saturated saline solution. The organic layer was dried over anhydrous magnesium sulfate and the solvent was evaporated in vacuo to give 0.42 g of 2-amino-N-(5-bromo-2-pyridyl)-3-hydroxybenzamide.

Then N,N-dimethylformamide was added to the insoluble matter obtained by filtration of the reaction solution, the mixture was filtered and the filtrate was concentrated in vacuo. Water was added to the resulting residue and the resulting precipitate was collected by filtration and dried in vacuo to give additional 3.28 g of the above compound. Although this contained impurities therein, it was not purified but used for the next reaction as it was.

REFERENCE EXAMPLE 13

2-Amino-N-(5-bromo-2-pyridyl)-3-hydroxybenzamide (1.99 g) and 990 mg of N-chlorosuccinimide were dissolved in 30 ml of N,N-dimethylformamide, the solution was stirred at 50° C. for 2 hours and the insoluble matter was filtered off. The solvent was evaporated in vacuo, water was added to the resulting residue and the precipitate was collected by filtration. This was dried in vacuo, purified by means of a silica gel column chromatography, water was added to the resulting crudely purified product and the resulting precipitate was collected by filtration and dried in vacuo to give 1.12 g of 2-amino-N-(5-bromo-2-pyridyl)-5-chloro-3-hydroxybenzamide.

EXAMPLE 1

2-Amino-5-bromo-N-(5-chloro-2-pyridyl)-3-hydroxybenzamide (5.14 g) and 2.83 g of 1-isopropylpiperidine-4-carboxylic acid were dissolved in 75 ml of N,N-dimethylformamide, then 4.33 g of 1-ethyl-3-dimethylaminopropylcarbodiimide hydrochloride and 3.04 g of 1-hydroxybenzotriazole were added thereto and the mixture was stirred at room temperature for 46 hours. The reaction solution was added to 750 ml of 1% aqueous solution of sodium bicarbonate and 200 ml of ethyl acetate were added thereto. Ethyl acetate was evaporated therefrom in vacuo and the resulting solid was collected by filtration and washed with water. The resulting solid was suspended in 100 ml of methanol and 10 ml of water and the suspension was stirred for one night. The resulting precipitate was collected by filtration and dried in vacuo to give 4.41 g of 4'-bromo-2'-[(5-chloro-2-pyridyl)carbamoyl]-6'-hydroxy-1-isopropylpiperidine-4-carboxanilide.

4'-Bromo-2'-[(5-chloro-2-pyridyl)carbamoyl]-6'-hydroxy-1-isopropylpiperidine-4-carboxanilide (480 mg) was suspended in 15 ml of chloroform, 15 ml of methanol and 10 ml of 1,4-dioxane, then 434 mg of 1,8-diazabicyclo[5,4,0]-7-undecene were added thereto and the mixture was stirred at room temperature for 2 hours. To the reaction solution were added 1.19 g of 1-bromo-1-deoxy-2,3,4,6-tetra-O-acetyl-α-D-galactopyranoside and the mixture was stirred at room temperature for 3 hours. To the reaction solution were added 868 mg of 1,8-diazabicyclo[5,4,0]-7-undecene, the mixture was stirred at room temperature for 3 hours and 1.19 g of 1-bromo-1-deoxy-2,3,4,6-tetra-O-acetyl-α-D-galactopyranoside were added thereto. After the mixture was stirred at room temperature for 12 hours, it was concentrated in vacuo. To the resulting residue were added 50 ml of water and the mixture was washed with 50 ml of chloroform and extracted with n-pentanol. The solvent was evaporated in vacuo and the resulting residue was purified by means of an ODS column chromatography using 0.1% aqueous solution of trifluoroacetic acid:acetonitrile (71:29) as an eluate to give 300 mg of 4-bromo-2'-[(5-chloro-2-pyridyl) carbamoyl]-6'-β-D-galactopyranosyloxy-1-isopropylpiperidine-4-carboxanilide trifluoroacetate.

Compounds of Examples 2, 4 and 8 were prepared by the same manner as in Example 1.

EXAMPLE 3

4'-Bromo-2'-[(5-chloro-2-pyridyl)carbamoyl]-6'-hydroxy-1-isopropylpiperidine-4-carboxanilide (500 mg) was suspended in 10 ml of chloroform, 10 ml of methanol and 5 ml of 1,4-dioxane, then 0.45 ml of 1,8-diazabicyclo[5,4,0]-7-undecene was added thereto and the mixture was stirred at room temperature for 1.5 hours. To the reaction solution were added 1.11 g of 2-acetamido-2,3,6-tri-O-acetyl-2-deoxy-α-D-glucopyranosyl bromide and the mixture was stirred at room temperature for 2 hours. To the reaction solution was added 0.90 ml of 1,8-diazabicyclo[5,4,0]-7-undecene, the mixture was stirred at room temperature for 30 minutes and 1.11 g of 2-acetamido-2,3,6-tri-O-acetyl-2-deoxy-α-D-glucopyranosyl bromide were added thereto. After the mixture was stirred at 60° C. for 2 hours and concentrated in vacuo. To the resulting residue were added 50 ml of water and the mixture was washed with 50 ml of chloroform and extracted with n-pentanol. The solvent was evaporated in vacuo and the resulting residue was purified by means of an ODS column chromatography using 0.1% aqueous solution of trifluoroacetic acid:acetonitrile (71:29) as an eluate to give 364 mg of 2'-(2-acetamido-2-deoxy-β-D-glucopyranosyloxy)-4'-bromo-6'-[(5-chloro-2-pyridyl)-carbamoyl]-1-isopropylpiperidine-4-carboxanilide trifluoroacetate.

EXAMPLE 5

3-Hydroxy-N$^1$-(4-methoxybenzoyl)-N$^2$-[4-(4-methyl-1,4-diazepan-1-yl)benzoyl]-1,2-phenylenediamine (300 mg), 377 mg of methyl 1-bromo-1-deoxy-2,3,4-tri-O-acetyl-α-D-glucopyranoside uronate and 225 mg of benzyltri-n-butylammonium bromide were suspended in 6 ml of chloroform, 1.9 ml of a 1N aqueous solution of sodium hydroxide were added thereto and the mixture was stirred at 60° C. for 2 hours. To the reaction solution were added 754 mg of methyl 1-bromo-1-deoxy-2,3,4-tri-O-acetyl-α-D-glucopyranoside uronate and the mixture was stirred at 60° C. for 3 hours. The reaction solution was extracted with chloroform and the extract was washed with a saturated aqueous saline. The resulting organic layer was dried over anhydrous sodium sulfate and concentrated in vacuo. The resulting residue was purified by means of a silica gel column chromatography using chloroform:methanol:a saturated aqueous ammonia (100:10:1) as an eluate to give 210 mg of crudely purified methyl (3-[(4-methoxybenzoyl) amino]-2-{[4-(4-methyl-1,4-diazepan-1-yl)benzoyl]amino}phenyl 2,3,4-tri-O-acetyl-β-D-glucopyranoside) uronate. The crudely purified product (220 mg) prepared in this method was dissolved in 5.5 ml of methanol and 2.7 ml of distilled water, 85 mg of sodium carbonate were added thereto and the mixture was stirred at room temperature for 2.5 hours and then at 60° C. for 2 hours. This was concentrated in vacuo and the resulting residue was purified by means of an ODS column chromatography using 0.1% aqueous solution of trifluoroacetic acid:tetrahydrofuran (70:30) as an eluate to give 150 mg of crudely purified 3-[(4-methoxybenzoyl)amino]-2-{[4-(4-methyl-1,4-diazepan-1-yl)benzoyl]amino}phenyl β-D-glucopyranoside uronic acid trifluoroacetate. The crudely purified product (310 mg) obtained by this method was purified by means of an HPLC (Develosil ODS-UG-5) using 0.1% aqueous solution of trifluoroacetic acid:tetrahydrofuran (75:25) as an eluate to give 115 mg of 3-[(4-methoxybenzoyl)amino]-2-{[4-(4-methyl-1,4-diazepan-1-yl) benzoyl]amino}phenyl β-D-glucopyranoside uronic acid trifluoroacetate.

EXAMPLE 6

4'-Chloro-2'-[(5-chloro-2-pyridyl)carbamoyl]-6'-hydroxy-1-isopropylpiperidine-4-carboxanilide (150 mg) was suspended in 1.6 ml of chloroform and 1.6 ml of methanol, then 152 mg of 1,8-diazabicyclo[5,4,0]-7-undecene was added thereto and the mixture was stirred at room temperature for 35 minutes. To the reaction solution were added 397 mg of methyl 1-bromo-1-deoxy-2,3,4-tri-O-acetyl-α-D-glucopyranoside uronate and the mixture was stirred at room temperature for 15 minutes and concentrated in vacuo. The resulting residue was purified by means of a silica gel column chromatography using chloroform:methanol:saturated aqueous ammonia (100:20:2) as an eluate to give 240 mg of a crudely purified product of methyl {5-chloro-3-[(5-chloro-2-pyridyl)carbamoyl]-2-[(1-isopropylpiperidine-4-carbonyl)amino]phenyl β-D-glucopyranoside} uronate. The crudely purified product (230 mg) was dissolved in 4.6 ml of methanol and 2.3 ml of distilled water, then 114 mg of sodium carbonate were added thereto and the mixture was stirred at room temperature for 1 hour. This was neutralized with trifluoroacetic acid and concentrated in vacuo. The resulting residue was purified by means of an OSD column chromatography using 0.1% aqueous solution of trifluoroacetic acid:acetonitrile (71:29) to give 86 mg of 5-chloro-3-[(5-chloro-2-pyridyl)carbamoyl]-2-[(1-isopropylpiperidine-4-carbonyl)amino]phenyl β-D-glucopyranoside uronic acid trifluoroacetate.

EXAMPLE 7

4'-Bromo-2'-[(5-chloro-2-pyridyl)carbamoyl]-6'-hydroxy-1-isopropylpiperidine-4-carbaxanilide (1.00 g) was suspended in 20 ml of chloroform and 20 ml of methanol, then 0.91 ml of 1,8-diazabicyclo[5,4,0]-7-undecene was added thereto and the mixture was stirred at room temperature for 2 hours. To the reaction solution were added 2.41 g of methyl 1-bromo-1-deoxy-2,3,4-tri-O-acetyl-α-D-glucopyranoside uronate and the mixture was stirred at room temperature for 16 hours. To the reaction solution were added 1.07 g of sodium carbonate and 20 ml of water and the mixture was stirred at room temperature for 23 hours and concentrated in vacuo. To the resulting residue were added 50 ml of 5% aqueous solution of sodium bicarbonate and the mixture was washed with chloroform and extracted with n-pentanol. The solvent was evaporated in vacuo and the resulting residue was purified by means of an ODS column chromatography using 0.1% aqueous solution of trifluoroacetic acid:acetonitrile (71:29) as an eluate to give 502 mg of 5-bromo-3-[(5-chloro-2-pyridyl)carbamoyl]-2-[1-isopropylpiperidine-4-carbonyl] amino]phenyl β-D-glucopyranoside uronic acid trifluoroacetate.

EXAMPLE 9

2-Amino-N-(5-chloro-2-pyridyl)-3-hydroxybenzamide (100 mg) and 80 mg of 1-isopropylpiperidine-4-carbaldehyde were suspended in 5 ml of toluene, then 10 mg of p-toluenesulfonic acid hydrate were added thereto and the mixture was heated to reflux for 2 hours together with removal of water by an azeotropic operation. After the solvent was evaporated in vacuo, 7 ml of acetic acid and 88 mg of a boran-trimethylamine complex were added to the resulting residue and the mixture was stirred at 70° C. for 15 hours. The solvent was evaporated in vacuo, a saturated aqueous solution of sodium hydrogen carbonate was added to the residue and the mixture was extracted with chloroform. The organic layer was dried over anhydrous magnesium sulfate, the solvent was evaporated in vacuo and the resulting residue was purified by means of a silica gel column chromatography. After addition of 1N hydrochloric acid and water to the resulting N-(5-chloro-2-pyridyl)-3-hydroxy-2-{[(1-isopropyl-4-piperidyl) methyl]amino}benzamide and the mixture was freeze-dried to give 102 mg of N-(5-chloro-2-pyridyl)-3-hydroxy-2-{[(1-isopropyl-4-piperidyl)methyl]amino}benzamide hydrochloride.

Compounds of Examples 10, 11, 12 and 13 were prepared by the same manner as Example 9.

EXAMPLE 14

4'-Chloro-3-hydroxy-2-nitrobenzanilide (1.43 g) was suspended in 50 ml of methanol, then 5 ml of distilled water, 2.80 g of reduced iron and 530 mg of ammonium chloride were added thereto and the mixture was stirred at 60° C. for 2 hours. The reaction was filtered through Celite and concentrated in vacuo. To the resulting residue was added a saturated saline solution and the mixture was extracted with chloroform. The organic layer was dried over magnesium sulfate and concentrated in vacuo. The resulting residue and 320 mg of 1-isopropylpyridine-4-carbaldehyde were suspended in 14 ml of toluene, then 37 mg of p-toluene sulfonic acid hydrate were added thereto and the mixture was heated to reflux for 24 hours together with removal of water by an azeotropic operation. This was concentrated in vacuo, to the resulting residue were added 14 ml of acetic acid and 350 mg of a boran-trimethylamine complex and the mixture was stirred at 70° C. for 17 hours. This was concentrated in vacuo, a 5% aqueous solution of sodium bicarbonate was added to the resulting residue and the mixture was extracted with chloroform. The organic layer was dried over magnesium sulfate and concentrated in vacuo. The resulting residue was purified by means of a silica gel column chromatography using chloroform:methanol:saturated aqueous ammonia (100:10:1) as an eluate to give 380 mg of crudely purified 4'-chloro-3-hydroxy-2-{[(1-isopropyl-4-piperidyl) methyl]amino}benzanilide. The crudely purified product (380 mg) was purified by means of an ODS column chromatography using 0.001N hydrochloric acid:methanol (10:3) as an eluate and then freeze-dried to give 162 mg of 4'-chloro-3-hydroxy-2-{[(1-isopropyl-4-piperidyl) methyl]amino}benzanilide hydrochloride.

Compounds of Examples 15 and 16 were prepared by the same manner as in Example 14.

EXAMPLE 17

To 612 mg of 1-isopropylpiperidine-4-carboxylic acid were added 5 ml of thionyl chloride and a few drops of N,N-dimethylformamide and the mixture was stirred at 60° C. for 1 hour. The solvent was evaporated in vacuo, to the resulting residue were added 465 mg of 2-amino-N-(5-chloro-2-pyridyl)-3-hydroxybenzamide and 20 ml of pyridine at 0° C. and the mixture was raised to room temperature and stirred at room temperature for one night. The solvent was evaporated in vacuo, a saturated aqueous solution of sodium hydrogen carbonate was added thereto and the mixture was extracted with chloroform. The organic layer was dried over anhydrous magnesium sulfate, the solvent was evaporated in vacuo and the resulting residue was purified by means of a silica gel column chromatography. The resulting crude product was suspended in ethanol, 1N hydrochloric acid was added thereto, the mixture was stirred and the resulting precipitate was collected by filtration and dried in vacuo to give 226 mg of 2'-[(5-chloro-2-pyridyl)carbamoyl]-6'-hydroxy-1-isopropylpiperidine-4-carboxanilide hydrochloride. Since this compound contained ethanol, it was made into an aqueous solution and freeze-dried and NMR was measured.

The compound of Example 20 was prepared by the same manner as in Example 17.

EXAMPLE 18

To 450 mg of 1-isopropylpiperidine-4-carboxylic acid were added 2.6 ml of thionyl chloride and 3 drops of N,N-dimethylformamide and the mixture was stirred at 60° C. for 30 minutes and concentrated in vacuo. To the resulting residue was added toluene and the mixture was concentrated in vacuo. After the above operation was carried out twice, 520 mg of 2-amino-5-chloro-N-(5-chloro-2-pyridyl)-3-hydroxybenzamide and 6 ml of pyridine were added thereto and the mixture was stirred at room temperature for 15 hours. After this was concentrated in vacuo, a 5% aqueous solution of sodium bicarbonate was added thereto and the mixture was extracted with chloroform. The organic layer was dried over anhydrous magnesium sulfate, the solvent was evaporated in vacuo and the resulting residue was purified by means of a silica gel column chromatography using chloroform:methanol:saturated aqueous ammonia (100:20:2) as an eluate to give 490 mg of crudely purified 4'-chloro-2'-[(5-chloro-2-pyridyl)carbamoyl]-6'-hydroxy-1-isopropylpiperidine-4-carboxanilide. The crudely purified product (310 mg) was purified by means of an ODS column chromatography using 0.001N hydrochloric acid:methanol (1:1) as an eluate and freeze-dried to give 301 mg of 4'-chloro-2'-[(5-chloro-2-pyridyl)carbamoyl]-6'-hydroxy-1-isopropylpiperidine-4-carboxanilide hydrochloride.

EXAMPLE 19

2-Amino-5-bromo-N-(5-chloro-2-pyridyl)-3-hydroxybenzamide (2.39 g) and 1.32 g of 1-isopropylpiperidine-4-carboxylic acid were dissolved in 35 ml of N,N-dimethylformamide, then 2.02 g of 1-ethyl-3-dimethylaminopropylcarbodiimide hydrochloride, 1.42 g of 1-hydroxybenzotriazole and 1.46 ml of triethylamine were added thereto and the mixture was stirred at room temperature for 22 hours. To the reaction solution were added 105 ml of water and 105 ml of ethyl acetate, the mixture was stirred at room temperature for 3 hours and the resulting precipitate was filtered, washed with ethyl acetate and water and dried in vacuo. The resulting solid was suspended in 60 ml of ethanol, 5 ml of 1N hydrochloric acid were added thereto and the mixture was stirred at room temperature for 30 hours. The resulting precipitate was filtered, washed with ethanol and dried in vacuo to give 1.35 g of 4'-bromo-2'-[(5-chloro-2-pyridyl)carbamoyl]-6'-hydroxy-1-isopropylpiperidine-4-carboxanilide hydrochloride.

The compound of Example 24 was prepared by the same manner as in Example 19.

EXAMPLE 21

To 374 mg of 1-isopropylpiperidine-4-carboxylic acid were added 3 ml of thionyl chloride and a few drops of N,N-dimethylformamide and the mixture was stirred at 80° C. for 30 minutes. The solvent was evaporated in vacuo, to the resulting residue were added 509 mg of 2-amino-N-(5-bromo-2-pyridyl)-5-chloro-3-hydroxybenzamide and 20 ml of pyridine at 0° C. and the mixture was raised up to room temperature and stirred at room temperature for one night. After the solvent was evaporated in vacuo, a saturated aqueous solution of sodium bicarbonate was added thereto and the mixture was extracted with chloroform. The organic layer was dried over anhydrous magnesium sulfate, the solvent was evaporated in vacuo and the resulting residue was purified by means of a silica gel column chromatography. 1N Hydrochloric acid and water were added to the resulting N-(5-bromo-2-pyridyl)-5-chloro-3-hydroxy-2-[(1-isopropylpiperidine-4-carbonyl)amino]benzamide and freeze-dried to give 602 mg of 2'-[(5-bromo-2-pyridyl)carbamoyl]-4'-chloro-6'-hydroxy-1-isopropylpiperidine-4-carboxanilide hydrochloride.

The compound of Example 22 was prepared by the same manner as in Example 21.

EXAMPLE 23

4'-Bromo-2'-[(5-chloro-2-pyridyl)carbamoyl]-6'-hydroxy-1-isopropylpiperidine-4-carbaxanilide (495 mg) was dissolved in 15 ml of N,N-dimethylformamide, 1.39 g of a trimethylamine-sulfur trioxide complex were added thereto and the mixture was stirred at 50° C. for 124 hours. A trimethylamine-sulfur trioxide complex (0.70 g) was further added thereto, the mixture was stirred at 50° C. for 21 hours, 30 ml of water were added thereto and the mixture was stirred at room temperature for 20 minutes. The resulting precipitate was filtered and washed with water. The resulting solid was suspended in methanol, stirred at room temperature for 12 hours, filtered, washed with methanol and dried in vacuo. The resulting solid was dissolved in 40 ml of methanol and 2 ml of a 1N aqueous solution of sodium hydroxide, the resulting filtrate was filtered off and the solvent was evaporated in vacuo. The resulting residue was dissolved in a mixed solvent of water and methanol again, the solution was neutralized with 0.1N hydrochloric acid and the resulting precipitate was filtered, washed with water and dried in vacuo. The resulting crudely purified product was dissolved in a diluted aqueous solution of sodium hydroxide and purified by means of an ODS column chromatography using acetonitrile:water (5:95~40:60) as an eluate. Acetonitrile contained in the fraction containing the aimed product was evaporated in vacuo and the resulting precipitate was filtered, washed with water and dried in vacuo to give 202 mg of 5-bromo-3-[(5-chloro-2-pyridyl) carbamoyl]-2-[(1-isopropylpiperidine-4-carbonyl) amino]phenyl hydrogen sulfate.

EXAMPLE 25

2-Amino-5-bromo-N-(5-chloro-2-pyridyl)-3-hydroxybenzamide (0.37 g) and 0.50 g of 1-isopropylpiperidine-4-carboxylic acid were dissolved in 10 ml of N,N-dimethylformamide, then 0.31 g of 1-ethyl-3-dimethylaminopropylcarbodiimide hydrochloride, 0.22 g of 1-hydroxybenzotriazole and 0.45 ml of triethylamine were added thereto and the mixture was stirred at room temperature for 18 hours and at 60° C. for 4 hours. The reaction solution was concentrated in vacuo, to the resulting residue were added 50 ml of chloroform and 50 ml of a 5% aqueous solution of sodium bicarbonate and the mixture was extracted with chloroform. The solvent was evaporated in vacuo and the resulting residue was washed with methanol and dried in vacuo to give 0.37 g of 4'-bromo-2'-[(5-chloro-2-pyridyl) carbamoyl]-6'-hydroxy-1-methanesulfonylpiperidine-4-carboxanilide.

Structural formulae and physical and chemical properties of the compounds of the above-mentioned Reference Examples and Examples are shown in Tables 3 to 4. Symbols in the tables have the following meanings.

| | |
|---|---|
| Rf: | Reference Example No. |
| Ex: | Example No. |
| structure: | Structural formula |
| salt: | salt |
| free: | free substance |
| DATA: | data of the properties |
| NMR: | nuclear magnetic resonance spectrum (internal standard: TMS) |
| FAB-MS: | mass spectrometric data |

The compounds shown in Tables 5 to 9 were easily prepared by nearly the same manner as the method mentioned in the above Examples and Preparation Examples or by applying some modifications which are obvious for persons skilled in the art to such a method.

In the structural formulae in Tables 3 to 4 and Table 9, "Y" means isopropyl, "O—" means methoxy, "-" means methyl and "$SO_2$—" means $SO_2$-methyl. The symbol "—" in the structural formulae in Tables 5 to 8 means a position of the bond. Some of the compounds described in Tables 3 and 4 may be a mixture of conformational isomers.

TABLE 3

| Rf | structure (salt) | DATA |
|---|---|---|
| 1 | 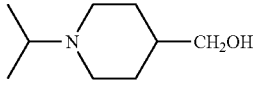 (free) | NMR(CDCl₃): δ: 1.04(6H, d, J = 6.0 Hz), 1.18-1.33(2H, m), 1.41-1.56(1H, m), 1.75(2H, d, J = 13.7 Hz), 2.11(2H, dt, $J_d$ = 9.3 Hz, $J_t$ = 11.6 Hz), 2.63-2.77(1H, m), 2.85-2.94(2H, m), 3.49(2H, d, J = 5.7 Hz) |
| 2 | 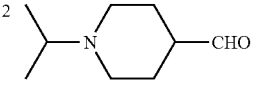 (free) | NMR(CDCl₃): δ: 1.04(6H, d, J = 6.6 Hz), 1.61-1.75(2H, m), 1.87-1.96(2H, m), 2.16-2.31(3H, m), 2.67-2.87(3H, m), 9.64(1H, d, J = 1.3 Hz) |
| 3 | 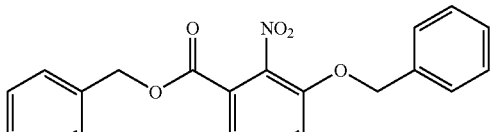 (free) | NMR(DMSO-d₆): δ: 5.33(4H, s), 7.31-7.45(10H, m), 7.61(1H, dd, J = 1.4 Hz, 7.5 Hz), 7.68(1H, t, J = 7.9 Hz), 7.74(1H, dd, J = 1.5 Hz, 8.2 Hz) |
| 4 | 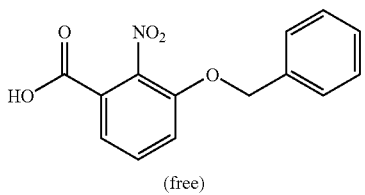 (free) | NMR(DMSO-d₆): δ: 5.32(2H, s), 7.31-7.44 (5H, m), 7.56(1H, dd, J = 1.4 Hz, 7.5 Hz), 7.68(1H, t, J = 7.9 Hz), 7.74(1H, dd, J = 1.5 Hz, 8.2 Hz) |
| 5 | 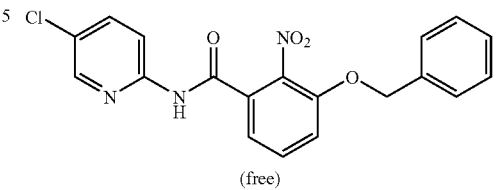 (free) | NMR(CDCl3): δ: 5.23(2H, s), 7.22-7.26(2H, m), 7.31-7.39 (5H, m), 7.46(1H, t, J = 8.3 Hz), 7.69(1H, dd, J = 2.7 Hz, 9.1 Hz), 8.03(1H, d, J = 2.9 Hz), 8.26(1H, d, J = 8.8 Hz), 9.01(1H, brs) |
| 6 | 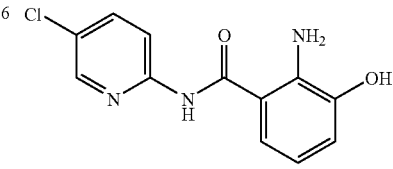 (free) | NMR(DMSO-d₆): δ: 5.93(2H, s), 6.44(1H, t, J = 7.9Hz), 6.82(1H, d, J = 7.7 Hz), 7.27(1H, d, J = 7.3 Hz), 7.93(1H, dd, J = 2.6 Hz, 9.0 Hz), 8.14(1H, d, J = 8.8 Hz), 8.41(1H, d, J = 2.4 Hz), 9.60(1H, s), 10.46(1H, s) |
| 7 | 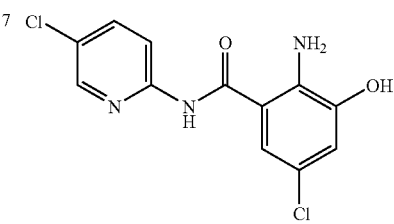 (free) | NMR(DMSO-d₆): δ: 6.04(2H, brs), 6.80(1H, d, J = 2.4 Hz), 7.36(1H, d, J = 2.0 Hz), 7.93(1H, dd, J = 2.5 Hz, 8.8 Hz), 8.11(1H, d, J = 9.3 Hz), 8.42(1H, d, J = 2.5 Hz), 10.16(1H, brs), 10.67(1H, s) |

TABLE 3-continued

| Rf | structure (salt) | DATA |
|---|---|---|
| 8 | 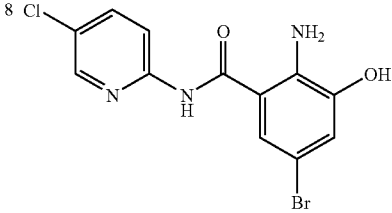 (free) | NMR(DMSO-d$_6$):<br>δ: 6.06(2H, brs), 6.90(1H, d, J = 2.0 Hz), 7.47(1H, d, J = 1.9 Hz), 7.93(1H, dd, J = 2.4 Hz, 8.8 Hz), 8.10(1H, d, J = 8.8 Hz), 8.42(1H, d, J = 2.4 Hz), 10.14(1H, brs), 10.68(1H, brs) |
| 9 | 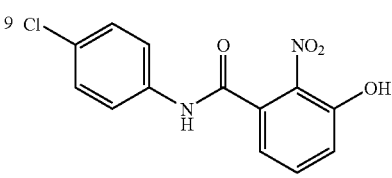 (free) | NMR(CDCl3):<br>δ: 7.08(1H, d, J = 7.1 Hz), 7.26(1H, d, J = 7.5 Hz), 7.34(2H, d, J = 8.8 Hz), 7.55(2H, d, J = 8.8 Hz), 7.57-7.62(1H, m), 7.79(1H, brs), 10.48(1H, brs) |
| 10 | 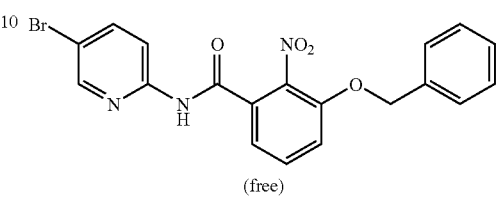 (free) | NMR(CDCl3):<br>δ: 5.24(2H, s), 7.22-7.27(2H, m), 7.30-7.41(5H, m), 7.47(1H, t, J = 8.1 Hz), 7.83(1H, dd, J = 2.4 Hz, 8.8 Hz), 8.14-8.17(1H, m), 8.22(1H, d, J = 8.8Hz), 8.90(1H, brs) |
| 11 | 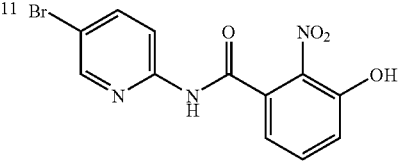 (free) | NMR(DMSO-d$_6$):<br>δ: 7.25(2H, d, J = 7.9 Hz), 7.50(1H, t, J = 8.0 Hz), 8.00-8.09(2H, m), 8.51(1H, dd, J = 0.7 Hz, 2.4 Hz), 11.24(1H, s), 11.37(1H, s) |
| 12 | 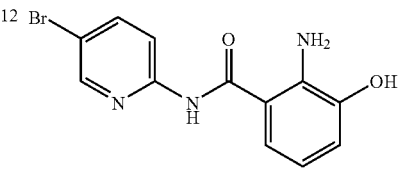 (free) | NMR(DMSO-d$_6$):<br>δ: 5.94(2H, brs), 6.44(1H, t, J = 8.1 Hz), 6.85(1H, dd, J = 1.0 Hz, 7.8 Hz), 7.27(1H, dd, J = 1.0 Hz, 8.3 Hz), 8.03(1H, dd, J = 2.4 Hz, 8.8 Hz), 8.09(1H, d, J = 8.8 Hz), 8.48(1H, d, J = 2.4 Hz), 10.38-1.52(1H, br) |
| 13 | 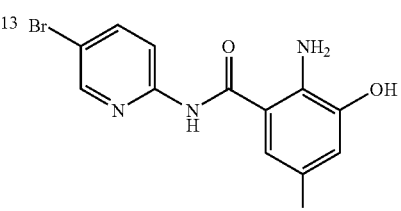 (free) | NMR(DMSO-d$_6$):<br>δ: 6.04(2H, brs), 6.80(1H, d, J = 2.2 Hz), 7.36(1H, d, J = 2.2 Hz), 8.05(2H, brs), 8.49(1H, d, J = 1.5 Hz), 10.16(1H, brs), 10.66(1H, s) |

TABLE 4

| Ex | structure (salt) | DATA |
|---|---|---|
| 1 | 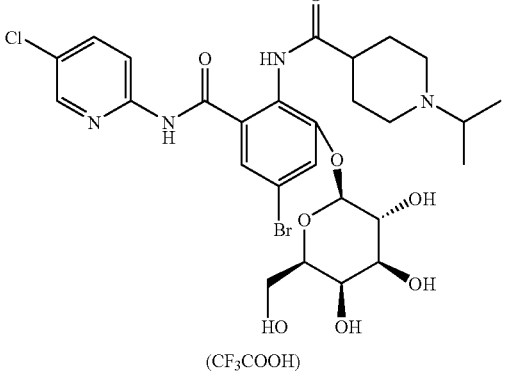<br>(CF₃COOH) | NMR(DMSO-d₆):<br>δ: 1.01-1.06(1.5H, d, J = 5.9 Hz), 1.23(4.5H, d, J = 6.4 Hz), 1.65-1.81(2H, m), 1.82-2.14(2H, m), 2.64-2.70(1H, m), 2.87-2.98(2H, m), 3.37-4.03(13H, m), 4.85(1H, d, J = 7.3 Hz), 7.42(1H, s), 7.50(1H, s), 7.90-7.95(1H, m), 8.09-8.13(1H, m), 8.39-8.41(1H, m), 8.84(0.75H, brs), 8.95(0.25H, brs), 9.46(0.25H, s), 9.50(0.75H, s), 10.78(0.75H, s), 10.92(0.25H, s)<br>FAB-MS(m/z): 659(M + H)⁺ |
| 2 | 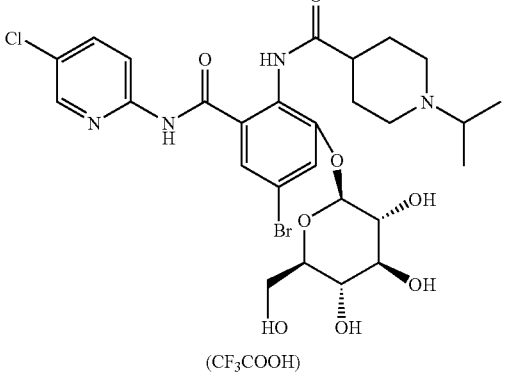<br>(CF₃COOH) | NMR(DMSO-d₆):<br>δ: 1.02(1.5H, d, J = 5.9 Hz), 1.23(4.5H, d, J = 6.4 Hz), 1.72-2.15(4H, m), 2.63-2.72(1H, m), 2.84-2.98(2H, m), 3.14-3.55(8H, m), 3.72-3.76(1H, m), 4.60-5.25(5H, m), 7.46(1H, d, J = 2.1 Hz), 7.51(1H, d, J = 1.6 Hz), 7.99(1H, dd, J = 1.3 Hz, 9.2 Hz), 8.06-8.10(1H, m), 8.34-8.36(1H, m), 8.75(0.75H, brs), 8.91(0.25H, brs), 9.24(0.75H, s), 9.27(0.25H, s), 10.39(0.75H, s), 10.53(0.25H, s)<br>FAB-MS(m/z): 659(M + H)⁺ |
| 3 | 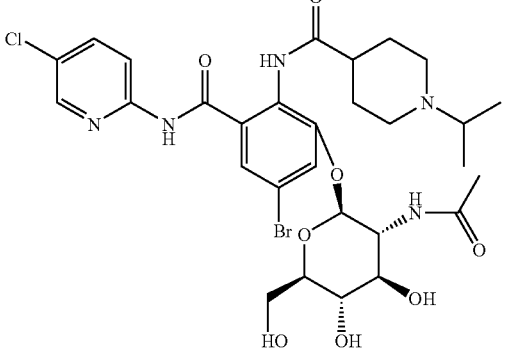<br>(CF₃COOH) | NMR(DMSO-d₆):<br>δ: 1.02-1.05(1.2H, m), 1.22(4.8H, d, J = 6.9 Hz), 1.62-2.16(7H, m), 2.68-2.79(1H, m), 2.82-3.02(3H, m), 3.13-3.23(2H, m), 3.38-4.13(9H, m), 4.97-4.99(1H, m), 7.37-7.39(1H, m), 7.43-7.45(1H, m), 7.90-7.94(1H, m), 7.99(1H, d, J = 8.3 Hz), 8.08-8.15(1H, m), 8.38(0.8H, d, J = 2.9 Hz), 8.41(0.2H, d, J = 2.9 Hz), 8.71-8.82(2H, m), 10.65(0.8H, s), 10.87(0.2H, s)<br>FAB-MS(m/z): 699(M + H)⁺ |

TABLE 4-continued

| Ex | structure (salt) | DATA |
|---|---|---|
| 4 | 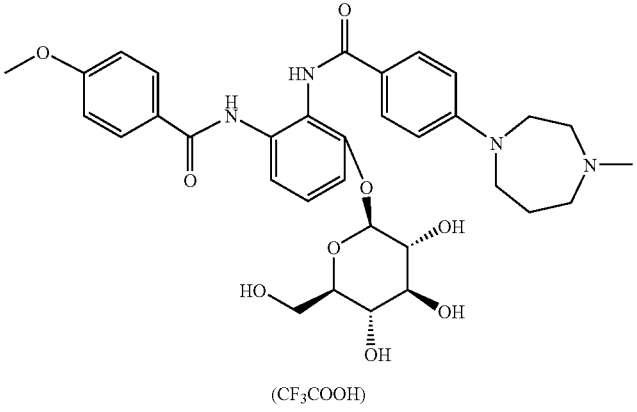<br>(CF$_3$COOH) | NMR(DMSO-d$_6$ + CD$_3$OD):<br>δ: 2.16-2.24(2H, m), 2.86(3H, s), 3.15-3.27(4H, m), 3.33-3.60(7H, m), 3.69-3.76(2H, m), 3.83(3H, s), 3.90-3.96(1H, m), 4.95(1H, d, J = 7.4 Hz), 6.89(2H, d, J = 8.8 Hz), 7.04(2H, d, J = 8.8 Hz), 7.11(1H, d, J = 8.3 Hz), 7.29-7.33(1H, m), 7.52(1H, d, J = 8.3 Hz), 7.86(2H, d, J = 8.8Hz), 7.93(2H, d, J = 8.8 Hz)<br>FAB-MS(m/z): 637(M + H)$^+$ |
| 5 | 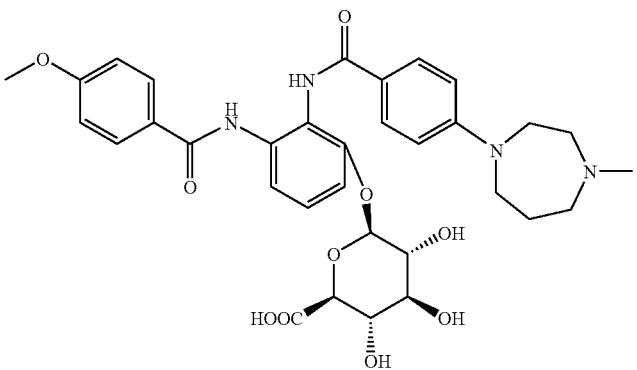<br>(CF$_3$COOH) | NMR(DMSO-d$_6$):<br>δ: 2.13-2.22(2H, m), 2.85(3H, d, J = 2.9 Hz), 3.12-3.27(3H, m), 3.33-3.73(7H, m), 3.82(3H, s), 3.88-3.97(1H, m), 4.00(1H, d, J = 9.3 Hz), 5.12(1H, d, J = 6.3 Hz), 5.29(3H, br s), 6.88(2H, d, J = 8.8 Hz), 7.03-7.06(3H, m), 7.29-7.33(1H, m), 7.48(1H, d, J = 7.8 Hz), 7.85(2H, d, J = 9.2 Hz), 7.89(2H, d, J = 8.8 Hz), 9.48(1H, s), 9.54(1H, brs), 9.88(1H, s), 12.83(1H, brs)<br>FAB-MS(m/z): 651(M + H)$^+$ |
| 6 | 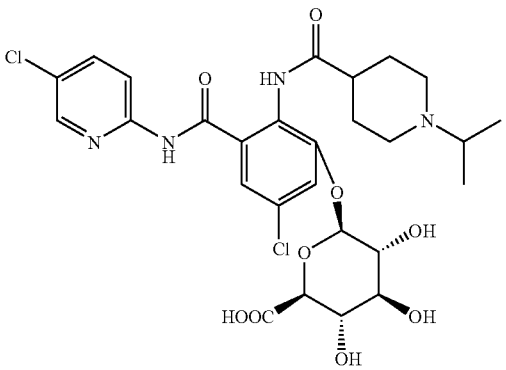<br>(CF$_3$COOH) | NMR(DMSO-d$_6$):<br>δ: 1.02-1.05(1.2H, m), 1.23(4.8H, d, J = 6.9 Hz), 1.66-2.13(4H, m), 2.62-3.46(9H, m), 4.02-4.05(1H, m), 5.12(1H, d, J = 6.8 Hz), 5.40(3H, brs), 7.31-7.33(1H, m), 7.38-7.40(1H, m), 7.91-7.95(1H, m), 8.08-8.13(1H, m), 8.40(0.75H, d, J = 2.5 Hz), 8.41(0.25H, d, J = 2.5 Hz), 8.76-8.92(1H, m), 9.46(0.2H, s), 9.49(0.8H, s), 10.79(0.8H, s), 10.93(0.2H, s), 12.88(1H, brs)<br>FAB-MS(m/z): 627(M + H)$^+$ |

TABLE 4-continued

| Ex | structure (salt) | DATA |
|---|---|---|
| 7 | (CF$_3$COOH) | NMR(DMSO-d$_6$):<br>δ: 1.02-1.04(1.2H, m), 1.22(4.8H, d, J = 6.4 Hz), 1.63-2.13(4H, m), 2.63-2.70(1H, m), 2.86-3.14(2H, m), 3.36-3.46(6H, m), 4.01-4.05(1H, m), 5.12(1H, d, J = 6.9 Hz), 5.18-5.54(3H, br), 7.43-7.45(1H, m), 7.47-7.51(1H, m), 7.92-7.95(1H, m), 8.08-8.14(1H, m), 8.38-8.42(1H, m), 8.80-9.00(1H, br), 9.44(0.2H, s), 9.48(0.8H, s), 10.79(0.8H, s), 10.93(0.2H, s), 12.85(1H, brs)<br>FAB-MS(m/z): 672(M + H)$^+$ |
| 8 | (CF$_3$COOH) | NMR(DMSO-d$_6$):<br>δ: 1.02-1.05(1.8H, m), 1.23(4.2H, d, J = 6.4 Hz), 1.66-2.14(4H, m), 2.62-2.74(1H, m), 2.83-3.16(4H, m), 3.28-3.33(5H, m), 3.37-3.47(3H, m), 3.61-3.72(2H, m), 4.97-4.99(1H, m), 5.30-6.20(3H, br), 7.42-7.44(1H, m), 7.47-7.49(1H, m), 7.92-7.95(1H, m), 8.07-8.13(1H, m), 8.38-8.42(1H, m), 8.89(0.3H, brs), 9.07(0.7H, brs), 9.43(0.3H, s), 9.47(0.7H, s), 10.76(0.7H, s), 10.91(0.3H, s)<br>FAB-MS(m/z): 673(M + H)$^+$ |
| 9 | (HCl) | NMR(DMSO-d$_6$):<br>δ: 1.27(6H, d, J = 6.3 Hz), 1.60-1.75(2H, m), 1.95-2.07(3H, m), 2.89(2H, q, J = 11.1 Hz), 3.18(2H, brs), 3.37(2H, d, J = 12.7 Hz), 3.85-3.95(1H, m), 7.15-7.30(2H, m), 7.32(1H, d, J = 7.3 Hz), 8.00(1H, dd, J = 2.5 Hz, 8.8 Hz), 8.19(1H, d, J = 8.8 Hz), 8.45(1H, d, J = 2.5 Hz), 10.23-10.40(1H, br), 10.82-11.32(1H, br), 11.53(1H, brs)<br>FAB-MS(m/z): 403(M + H)$^+$ |
| 10 | (HCl) | NMR(DMSO-d$_6$):<br>δ: 1.23(6H, d, J = 6.9 Hz), 1.45-1.58(2H, m), 1.75-1.91(3H, m), 2.83(2H, q, J = 11.1 Hz), 3.00(2H, d, J = 6.4 Hz), 3.27-3.40(3H, m), 7.08(1H, d, J = 1.9 Hz), 7.20(1H, d, J = 2.4 Hz), 7.97(1H, dd, J = 2.7 Hz, 8.8 Hz), 8.18(1H, d, J = 9.3 Hz), 8.43(1H, d, J = 2.4 Hz), 9.94(1H, brs), 10.60-10.95(1H, br), 11.51(1H, s)<br>FAB-MS(m/z): 437(M + H)$^+$ |
| 11 | (HCl) | NMR(DMSO-d$_6$):<br>δ: 1.25(6H, d, J = 6.4 Hz), 1.50-1.67(2H, m), 1.75-2.02(3H, m), 2.86(2H, q, J = 11.1 Hz), 3.06(2H, brs), 3.30-3.45(3H, m), 7.04(1H, brs), 7.14(1H, brs), 7.29(1H, d, J = 7.8 Hz), 8.08(1H, dd, J = 2.5 Hz, 9.3 Hz), 8.16(1H, d, J = 8.8 Hz), 8.50(1H, d, J = 2.4 Hz), 10.09(1H, brs), 10.20-10.90(1H, br), 11.60(1H, brs)<br>FAB-MS(m/z): 449(M + H)$^+$ |

TABLE 4-continued

| Ex | structure (salt) | DATA |
|---|---|---|
| 12 | (5-bromopyridin-2-yl / 5-chloro, 3-OH benzamide with (1-isopropylpiperidin-4-yl)methylamino) (HCl) | NMR(DMSO-d$_6$):<br>δ: 1.23(6H, d, J = 6.9 Hz), 1.44-1.58(2H, m), 1.75-2.00(3H, m), 2.83(2H, q, J = 11.2 Hz), 3.01(2H, d, J = 6.3 Hz), 3.27-3.43(3H, m), 7.07(1H, brs), 7.20(1H, d, J = 2.4 Hz), 8.08(1H, dd, J = 2.4 Hz, 8.8 Hz), 8.13(1H, d, J = 8.8 Hz), 8.50(1H, d, J = 1.9 Hz), 9.82(1H, brs), 10.77(1H, brs), 11.50(1H, s)<br>FAB-MS(m/z): 483(M + H)$^+$ |
| 13 | (5-methylpyridin-2-yl benzamide analog) (HCl) | NMR(DMSO$_6$):<br>δ: 1.26(6H, d, J = 6.8 Hz), 1.57-1.68(2H, m), 1.83-1.95(3H, m), 2.30(3H, s), 2.77-2.89(2H, m), 3.05(2H, d, J = 6.3 Hz), 3.28-3.40(3H, m), 6.91(1H, t, J = 7.8 Hz), 7.07(1H, dd, J = 1.4 Hz, 7.8 Hz), 7.31(1H, dd, J = 1.4 Hz, 7.8 Hz), 7.74(1H, dd, J = 2.0 Hz, 8.3 Hz), 8.03(1H, d, J = 8.3 Hz), 8.21(1H, d, J = 2.0 Hz), 10.08(1H, brs)<br>FAB-MS(m/z): 383(M + H)$^+$ |
| 14 | (4-chlorophenyl benzamide analog) (HCl) | NMR(DMSO-d$_6$):<br>δ: 1.22-1.26(6H, m), 1.49-1.61(2H, m), 1.74-1.92(3H, m), 2.78-2.87(2H, m), 3.10(2H, d, J = 6.9 Hz), 3.25-3.35(3H, m), 6.75-6.79(1H, m), 6.95-6.97(1H, m), 7.07-7.09(1H, m), 7.35-7.39(2H, m), 7.72-7.75(2H, m), 9.65(1H, brs), 10.33(1H, s)<br>FAB-MS(m/z): 402(M + H)$^+$ |
| 15 | (3-methylphenyl benzamide analog) (HCl) | NMR(DMSO-d$_6$):<br>δ: 1.23(6H, d, J = 6.4 Hz), 1.47-1.62(2H, m), 1.80-1.94(3H, m), 2.31(3H, s), 2.84(2H, q, J = 11.2 Hz), 3.14(2H, d, J = 4.9 Hz), 3.27-3.42(3H, m), 6.93(1H, d, J = 7.3 Hz), 7.00-7.18(3H, m), 7.23(1H, t, J = 7.8 Hz), 7.50(1H, d, J = 8.3 Hz), 7.56(1H, s), 9.72-9.90(1H, br), 10.33-10.48(1H, br)<br>FAB-MS(m/z): 382(M + H)$^+$ |
| 16 | (4-methoxyphenyl benzamide analog) (HCl) | NMR(DMSO-d$_6$):<br>δ: 1.18-1.26(6H, m), 1.42-1.63(2H, m), 1.68-2.04(3H, m), 2.77-2.93(2H, m), 3.00-3.70(5H, m), 3.75(3H, m), 6.84-7.24(5H, m), 7.62(2H, d, J = 8.8 Hz), 9.67(1H, brs), 10.33(1H, brs)<br>FAB-MS(m/z): 398(M + H)$^+$ |
| 17 | (5-chloropyridin-2-yl with piperidine-4-carboxamide analog) (HCl) | NMR(DMSO-d$_6$):<br>δ: 1.06(1.5H, d, J = 6.4 Hz), 1.24(4.5H, d, J = 6.3 Hz), 1.75-2.10(4H, m), 2.63-3.45(6H, m), 7.01-7.09(2H, m), 7.12-7.20(1H, m), 7.90-7.96(1H, m), 8.13(0.25H, d, J = 8.3 Hz), 8.15(0.75H, d, J = 8.8 Hz), 8.37(0.75H, d, J = 3.0 Hz), 8.39(0.25H, d, J = 2.5 Hz), 9.20-9.30(0.75H, br), 9.41(0.75H, s), 9.46(0.25H, s), 9.74-9.80(0.25H, br), 9.84(0.75H, s), 9.85(0.25H, s), 10.39(0.75H, s), 10.59(0.25H, s),<br>FAB-MS(m/z): 417(M + H)$^+$ |

TABLE 4-continued

| Ex | structure (salt) | DATA |
|---|---|---|
| 18 | (HCl) | NMR(DMSO-d₆):<br>δ: 1.05(1.8H, d, J = 6.8 Hz), 1.25(4.2H, d, J = 6.3 Hz), 1.81-2.18(4H, m), 2.63-3.26(4H, m), 3.34-3.44(2H, m), 7.05-7.06(1H, m), 7.15-7.17(1H, m), 7.91-7.96(1H, m), 8.09-8.13(1H, m), 8.37-8.41(1H, m), 9.47(0.7H, s), 9.56(0.3H, s), 10.45-10.68(1.7H, m), 10.41(0.3H, brs), 10.61(0.7H, s), 10.81(0.3H, s)<br>FAB-MS(m/z): 451(M + H)⁺ |
| 19 | (HCl) | NMR(DMSO-d₆):<br>δ: 1.04(1.8H, d, J = 6.8 Hz), 1.24(4.2H, d, J = 6.3 Hz), 1.74-2.12(4H, m), 2.60-3.45(6H, m), 7.15-7.19(1H, m), 7.23-7.27(1H, m), 7.89-7.97(1H, m), 8.07-8.14(1H, m), 8.35-8.41(1H, m), 9.39-9.55(1.7H, m), 9.98-10.10(0.3H, br), 10.44-10.50(1H, m), 10.62(0.7H, s), 10.81(0.3H, s)<br>FAB-MS(m/z): 497(M + H)⁺ |
| 20 | (HCl) | NMR(DMSO-d₆):<br>δ: 1.06(1.5H, d, J = 6.4 Hz), 1.24(4.5H, d, J = 6.3 Hz), 1.75-2.08(4H, m), 2.65-3.42(6H, m), 7.01-7.08(2H, m), 7.12-7.19(1H, m), 8.01-8.13(2H, m), 8.44(0.75H, d, J = 2.5 Hz), 8.46(0.25H, d, J = 2.4 Hz), 9.25(0.75H, brs), 9.41(0.75H, s), 9.46(0.25H, s), 9.77(0.25H, brs), 9.84(0.75H, s), 9.86(0.25H, s), 10.39(0.75H, s), 10.58(0.25H, s)<br>FAB-MS(m/z): 461(M + H)⁺ |
| 21 | (HCl) | NMR(DMSO-d₆):<br>δ: 1.03(1.2H, d, J = 6.8 Hz), 1.23(4.8H, d, J = 6.3 Hz), 1.68-2.10(4H, m), 2.60-3.30(6H, m), 7.05-7.09(2H, m), 8.01-8.10(2H, m), 8.44-8.48(1H, m), 8.98(0.8H, brs), 9.30-9.52(1.2H, m), 10.38(0.8H, s), 10.40(0.2H, s), 10.62(0.8H, s), 10.81(0.2H, s)<br>FAB-MS(m/z): 497(M + H)⁺ |
| 22 | (HCl) | NMR(DMSO-d₆):<br>δ: 1.04(1.5H, d, J = 6.3 Hz), 1.26(4.5H, d, J = 6.9 Hz), 1.83-2.22(4H, m), 2.33(0.8H, s), 2.35(2.2H, s), 2.64-3.23(4H, m), 3.32-3.40(2H, m), 7.11-7.13(1H, m), 7.22-7.25(1H, m), 7.85-7.91(1H, m), 7.95-8.08(1H, m), 8.25-8.29(1H, m), 9.65(0.75H, s), 9.70(0.25H, s), 10.12(0.75H, brs), 10.58(0.25H, brs), 10.79(1H, brs), 11.36(0.25H, s), 11.49(0.75H, s)<br>FAB-MS(m/z): 431(M + H)⁺ |

TABLE 4-continued

| Ex | structure (salt) | DATA |
|---|---|---|
| 23 | 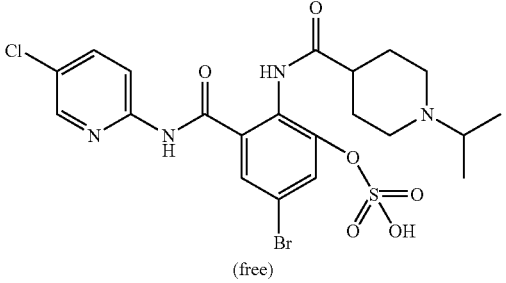 (free) | NMR(DMSO-$d_6$): δ: 1.08(1.2H, d, J = 6.8 Hz), 1.22(4.8H, d, J = 6.8 Hz), 1.65-2.21(4H, m), 2.55-3.50(6H, m), 7.45-7.50(1H, m), 7.62-7.70(1H, m), 7.89-7.95(1H, m), 8.05-8.14(1H, m), 8.36-8.42(1H, m), 8.63-8.79(1H, br), 9.51(0.8H, s), 9.67(0.2 H, s), 10.78(0.8H, s), 10.92(0.2H, s) FAB-MS(m/z): 575(M + H)$^+$ |
| 24 | 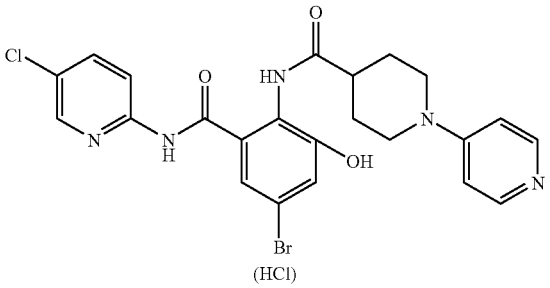 (HCl) | NMR(DMSO-$d_6$): δ: 1.46-1.57(2H, m), 1.82-1.90(2H, m), 2.81-2.90(1H, m), 3.20-3.28(2H, m), 4.08-4.14(2H, m), 7.13-7.16(3H, m), 7.27(1H, d, J = 1.5 Hz), 7.88(1H, dd, J = 1.5 Hz, 8.8 Hz), 8.09(1H, d, J = 9.3 Hz), 8.21(2H, d, J = 7.3 Hz), 8.33(1H, d, J = 2.4 Hz), 9.42(1H, s), 10.50(1H, s), 10.56(1H, s), 13.49(1H, s) FAB-MS(m/z): 532(M + H)$^+$ |
| 25 | 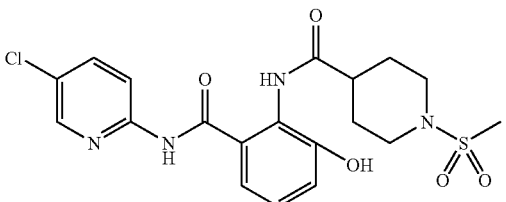 (free) | NMR(DMSO-$d_6$): δ: 1.44-1.55(2H, m), 1.75-1.81(2H, m), 2.48-2.54(1H, m), 2.66-2.74(2H, m), 2.82(3H, s), 3.45-3.51(2H, m), 7.16-7.19(2H, m), 7.93(1H, dd, J = 3.0 Hz, 8.8 Hz), 8.12(1H, d, J = 8.8 Hz), 8.38(1H, d, J = 2.4 Hz), 9.32(1H, brs), 10.28(1H, brs), 10.57(1H, s) FAB-MS(m/z): 451(M + H)$^+$ |

TABLE 5

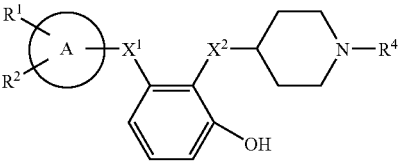

| No. | R¹/R²/A | X¹ | X² | R⁴ |
|---|---|---|---|---|
| 1 |  | —NH—C(=O)— | —C(=O)—NH— | —CH(CH$_3$)$_2$ |
| 2 |  | —NH—C(=O)— | —CH$_2$—NH— | —CH(CH$_3$)$_2$ |
| 3 | 5-Cl-pyridin-2-yl | —C(=O)—NH— | —C(=O)—NH— | —CH(CH$_3$)$_2$ |
| 4 |  | —C(=O)—NH— | —NH—C(=O)— | —CH(CH$_3$)$_2$ |
| 5 |  | —C(=O)—NH— | —NH—CH$_2$— | —CH(CH$_3$)$_2$ |
| 6 |  | —C(=O)—NH— | —CH$_2$—NH— | —CH(CH$_3$)$_2$ |
| 7 |  | —NH—C(=O)— | —NH—C(=O)— | —(CH$_2$)$_2$CH$_3$ |
| 8 |  | —NH—C(=O)— | —NH—CH$_2$— | —(CH$_2$)$_2$CH$_3$ |
| 9 |  | —NH—C(=O)— | —NH—C(=O)— | —CH$_2$CH$_3$ |
| 10 |  | —NH—C(=O)— | —NH—CH$_2$— | —CH$_2$CH$_3$ |
| 11 |  | —NH—C(=O)— | —NH—C(=O)— | —CH$_3$ |
| 12 |  | —NH—C(=O)— | —NH—CH$_2$— | —CH$_3$ |

TABLE 5-continued

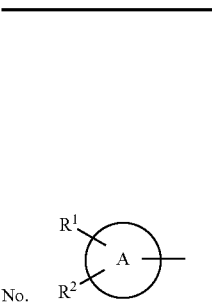

| No. | R¹/R² A | X¹ | X² | R⁴ |
|---|---|---|---|---|
| 13 | Br—pyridine-Me | —NH—C(=O)— | —NH—C(=O)— | —CH₃ |
| 14 | | —C(=O)—NH— | —NH—C(=O)— | —CH(CH₃)₂ |
| 15 | | —C(=O)—NH— | —NH—CH₂— | —CH(CH₃)₂ |
| 16 | F—pyridine-Me | —NH—C(=O)— | —NH—C(=O)— | —CH(CH₃)₂ |
| 17 | | —NH—C(=O)— | —NH—CH₂— | —CH(CH₃)₂ |
| 18 | | —C(=O)—NH— | —NH—C(=O)— | —CH(CH₃)₂ |
| 19 | | —C(=O)—NH— | —NH—CH₂— | —CH(CH₃)₂ |
| 20 | Me—pyridine-Me | —NH—C(=O)— | —NH—C(=O)— | —CH(CH₃)₂ |
| 21 | | —NH—C(=O)— | —NH—CH₂— | —(CH₃)₂ |
| 22 | MeO—pyridine-Me | —NH—C(=O)— | —NH—C(=O)— | —CH(CH₃)₂ |
| 23 | | —NH—C(=O)— | —NH—CH₂— | —CH(CH₃)₂ |
| 24 | Cl—pyridine-Me | —NH—C(=O)— | —NH—C(=O)— | —CH(CH₃)₂ |
| 25 | | —NH—C(=O)— | —NH—CH₂— | —CH(CH₃)₂ |
| 26 | Cl—thiazole-Me | —NH—C(=O)— | —NH—C(=O)— | —CH(CH₃)₂ |
| 27 | | —NH—C(=O)— | —NH—CH₂— | —CH(CH₃)₂ |
| 28 | | —C(=O)—NH— | —NH—C(=O)— | —CH(CH₃)₂ |
| 29 | | —C(=O)—NH— | —NH—CH₂— | —CH(CH₃)₂ |
| 30 | Cl—phenyl- | —NH—C(=O)— | —NH—CH₂— | —CH₂CH₃ |
| 31 | | —C(=O)—NH— | —NH—CH₂— | —CH(CH₃)₂ |
| 32 | F—phenyl- | —NH—C(=O)— | —NH—CH₂— | —CH(CH₃)₂ |
| 33 | | —C(=O)—NH— | —NH—CH₂— | —CH(CH₃)₂ |
| 34 | MeO—phenyl- | —C(=O)—NH— | —NH—CH₂— | —CH₂CH₃ |
| 35 | | —C(=O)—NH— | —NH—CH₂— | —CH(CH₃)₂ |
| 36 | Me—phenyl- | —NH—C(=O)— | —NH—CH₂— | —CH₂CH₃ |
| 37 | | —C(=O)—NH— | —NH—CH₂— | —CH(CH₃)₂ |
| 38 | FH₂C—O—phenyl- | —NH—C(=O)— | —NH—CH₂— | —CH(CH₃)₂ |
| 39 | | —C(=O)—NH— | —NH—CH₂— | —CH(CH₃)₂ |
| 40 | F₂HC—O—phenyl- | —NH—C(=O)— | —NH—CH₂— | —CH(CH₃)₂ |
| 41 | | —C(=O)—NH— | —NH—CH₂— | —CH(CH₃)₂ |

TABLE 5-continued

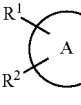

| No. | R¹–A–R² (A ring) | X¹ | X² | R⁴ |
|---|---|---|---|---|
| 42 | MeO-pyridyl-F | —NH—C(=O)— | —NH—CH₂— | —CH(CH₃)₂ |
| 43 | MeO-pyridyl-F | —C(=O)—NH— | —NH—CH₂— | —CH(CH₃)₂ |
| 44 | Cl-pyridazine | —NH—C(=O)— | —NH—C(=O)— | —CH(CH₃)₂ |
| 45 | Cl-pyridazine | —NH—C(=O)— | —NH—CH₂— | —CH(CH₃)₂ |
| 46 | Cl-pyridazine | —C(=O)—NH— | —NH—C(=O)— | —CH(CH₃)₂ |
| 47 | Cl-pyridazine | —C(=O)—NH— | —NH—CH₂— | —CH(CH₃)₂ |
| 48 | Cl-pyrimidine | —NH—C(=O)— | —NH—C(=O)— | —CH(CH₃)₂ |
| 49 | Cl-pyrimidine | —NH—C(=O)— | —NH—CH₂— | —CH(CH₃)₂ |
| 50 | Cl-pyrimidine | —C(=O)—NH— | —NH—C(=O)— | —CH(CH₃)₂ |
| 51 | Cl-pyrimidine | —C(=O)—NH— | —NH—CH₂— | —CH(CH₃)₂ |
| 52 | Cl-thiazole | —NH—C(=O)— | —NH—C(=O)— | —CH(CH₃)₂ |
| 53 | Cl-thiazole | —NH—C(=O)— | —NH—CH₂— | —CH(CH₃)₂ |
| 54 | Cl-thiazole | —C(=O)—NH— | —NH—C(=O)— | —CH(CH₃)₂ |
| 55 | Cl-thiazole | —C(=O)—NH— | —NH—CH₂— | —CH(CH₃)₂ |
| 56 | Cl-oxazole | —NH—C(=O)— | —NH—C(=O)— | —CH(CH₃)₂ |
| 57 | Cl-oxazole | —NH—C(=O)— | —NH—CH₂— | —CH(CH₃)₂ |
| 58 | Cl-oxazole | —C(=O)—NH— | —NH—C(=O)— | —CH(CH₃)₂ |
| 59 | Cl-oxazole | —C(=O)—NH— | —NH—CH₂— | —CH(CH₃)₂ |

TABLE 6

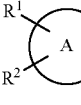

| No. | R¹–A–R² (A ring) | X¹ | X² | R⁴ |
|---|---|---|---|---|
| 60 | Cl-pyridyl | —NH—C(=O)— | —C(=O)—NH— | —CH(CH₃)₂ |
| 61 | Cl-pyridyl | —NH—C(=O)— | —CH₂—NH— | —CH(CH₃)₂ |
| 62 | Cl-pyridyl | —C(=O)—NH— | —C(=O)—NH— | —CH(CH₃)₂ |
| 63 | Cl-pyridyl | —C(=O)—NH— | —NH—C(=O)— | —CH(CH₃)₂ |
| 64 | Cl-pyridyl | —C(=O)—NH— | —NH—CH₂— | —CH(CH₃)₂ |
| 65 | Cl-pyridyl | —C(=O)—NH— | —CH₂—NH— | —CH(CH₃)₂ |
| 66 | Cl-pyridyl | —NH—C(=O)— | —NH—C(=O)— | —(CH₂)₂CH₃ |
| 67 | Cl-pyridyl | —NH—C(=O)— | —NH—CH₂— | —(CH₂)₂CH₃ |
| 68 | Cl-pyridyl | —NH—C(=O)— | —NH—C(=O)— | —CH₂CH₃ |
| 69 | Cl-pyridyl | —NH—C(=O)— | —NH—CH₂— | —CH₂CH₃ |
| 70 | Cl-pyridyl | —NH—C(=O)— | —NH—C(=O)— | —CH₃ |
| 71 | Cl-pyridyl | —NH—C(=O)— | —NH—CH₂— | —CH₃ |

TABLE 6-continued

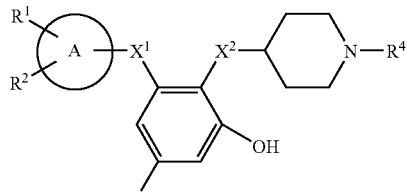

| No. | A with R¹,R² | X¹ | X² | R⁴ |
|---|---|---|---|---|
| 72 | 5-Br, 2-Me pyridine | —NH—C(=O)— | —NH—C(=O)— | —CH₃ |
| 73 |  | —NH—C(=O)— | —NH—C(=O)— | —CH₂CH₃ |
| 74 |  | —C(=O)—NH— | —NH—C(=O)— | —CH(CH₃)₂ |
| 75 |  | —C(=O)—NH— | —NH—CH₂— | —CH(CH₃)₂ |
| 76 | 5-F, 2-Me pyridine | —NH—C(=O)— | —NH—C(=O)— | —CH(CH₃)₂ |
| 77 |  | —NH—C(=O)— | —NH—CH₂— | —CH(CH₃)₂ |
| 78 |  | —C(=O)—NH— | —NH—C(=O)— | —CH(CH₃)₂ |
| 79 |  | —C(=O)—NH— | —NH—CH₂— | —CH(CH₃)₂ |
| 80 | 5-Me, 2-Me pyridine | —NH—C(=O)— | —NH—C(=O)— | —CH₂CH₃ |
| 81 |  | —NH—C(=O)— | —NH—CH₂— | —CH(CH₃)₂ |
| 82 | 5-MeO, 2-Me pyridine | —NH—C(=O)— | —NH—C(=O)— | —CH(CH₃)₂ |
| 83 |  | —NH—C(=O)— | —NH—CH₂— | —CH(CH₃)₂ |
| 84 | 2-Cl, 5-Me pyridine | —NH—C(=O)— | —NH—C(=O)— | —CH(CH₃)₂ |
| 85 |  | —NH—C(=O)— | —NH—CH₂— | —CH(CH₃)₂ |
| 86 | 5-Cl, 2-Me thiazole | —NH—C(=O)— | —NH—C(=O)— | —CH(CH₃)₂ |
| 87 |  | —NH—C(=O)— | —NH—CH₂— | —CH(CH₃)₂ |
| 88 |  | —C(=O)—NH— | —NH—C(=O)— | —CH(CH₃)₂ |
| 89 |  | —C(=O)—NH— | —NH—CH₂— | —CH(CH₃)₂ |
| 90 | 4-Cl phenyl | —NH—C(=O)— | —NH—CH₂— | —CH(CH₃)₂ |
| 91 |  | —C(=O)—NH— | —NH—CH₂— | —CH(CH₃)₂ |
| 92 | 4-F phenyl | —NH—C(=O)— | —NH—CH₂— | —CH(CH₃)₂ |
| 93 |  | —C(=O)—NH— | —NH—CH₂— | —CH(CH₃)₂ |
| 94 | 4-MeO phenyl | —NH—C(=O)— | —NH—CH₂— | —CH(CH₃)₂ |
| 95 |  | —C(=O)—NH— | —NH—CH₂— | —CH(CH₃)₂ |
| 96 | 3-Me phenyl | —NH—C(=O)— | —NH—CH₂— | —CH(CH₃)₂ |
| 97 |  | —C(=O)—NH— | —NH—CH₂— | —CH(CH₃)₂ |
| 98 | 4-(FH₂C—O) phenyl | —NH—C(=O)— | —NH—CH₂— | —CH(CH₃)₂ |
| 99 |  | —C(=O)—NH— | —NH—CH₂— | —CH(CH₃)₂ |
| 100 | 4-(F₂HC—O) phenyl | —NH—C(=O)— | —NH—CH₂— | —CH(CH₃)₂ |
| 101 |  | —C(=O)—NH— | —NH—CH₂— | —CH(CH₃)₂ |

TABLE 6-continued

[Structure: A ring with R¹, R² substituents connected via X¹ to a benzene ring (with OH and Cl substituents), which is connected via X² to a piperidine with N—R⁴]

| No. | [A ring with R¹, R²] | X¹ | X² | R⁴ |
|---|---|---|---|---|
| 102 | MeO—[benzene ring with F]— | —NH—C(=O)— | —NH—CH₂— | —CH(CH₃)₂ |
| 103 | | —C(=O)—NH— | —NH—CH₂— | —CH(CH₃)₂ |
| 104 | Cl—[pyridazine]— | —NH—C(=O)— | —NH—C(=O)— | —CH(CH₃)₂ |
| 105 | | —NH—C(=O)— | —NH—CH₂— | —CH(CH₃)₂ |
| 106 | | —C(=O)—NH— | —NH—C(=O)— | —CH(CH₃)₂ |
| 107 | | —C(=O)—NH— | —NH—CH₂— | —CH(CH₃)₂ |
| 108 | Cl—[pyrimidine]— | —NH—C(=O)— | —NH—C(=O)— | —CH(CH₃)₂ |
| 109 | | —NH—C(=O)— | —NH—CH₂— | —CH(CH₃)₂ |
| 110 | | —C(=O)—NH— | —NH—C(=O)— | —CH(CH₃)₂ |
| 111 | | —C(=O)—NH— | —NH—CH₂— | —CH(CH₃)₂ |
| 112 | Cl—[thiazole]— | —NH—C(=O)— | —NH—C(=O)— | —CH(CH₃)₂ |
| 113 | | —NH—C(=O)— | —NH—CH₂— | —CH(CH₃)₂ |
| 114 | | —C(=O)—NH— | —NH—C(=O)— | —CH(CH₃)₂ |
| 115 | Cl—[oxazole]— | —NH—C(=O)— | —NH—C(=O)— | —CH(CH₃)₂ |
| 116 | | —NH—C(=O)— | —NH—CH₂— | —CH(CH₃)₂ |
| 117 | | —C(=O)—NH— | —NH—C(=O)— | —CH(CH₃)₂ |

TABLE 7

[Structure: same as above but with Br instead of Cl on the benzene ring]

| No. | [A ring with R¹, R²] | X¹ | X² | R⁴ |
|---|---|---|---|---|
| 118 | Cl—[pyridine]— | —NH—C(=O)— | —C(=O)—NH— | —CH(CH₃)₂ |
| 119 | | —NH—C(=O)— | —CH₂—NH— | —CH(CH₃)₂ |
| 120 | | —C(=O)—NH— | —C(=O)—NH— | —CH(CH₃)₂ |
| 121 | | —C(=O)—NH— | —NH—C(=O)— | —CH(CH₃)₂ |
| 122 | | —C(=O)—NH— | —NH—CH₂— | —CH(CH₃)₂ |
| 123 | | —C(=O)—NH— | —CH₂—NH— | —CH(CH₃)₂ |
| 124 | | —NH—C(=O)— | —NH—C(=O)— | —(CH₂)₂CH₃ |
| 125 | | —NH—C(=O)— | —NH—CH₂— | —(CH₂)₂CH₃ |
| 126 | | —NH—C(=O)— | —NH—C(=O)— | —CH₂CH₃ |
| 127 | | —NH—C(=O)— | —NH—CH₂— | —CH₂CH₃ |
| 128 | | —NH—C(=O)— | —NH—C(=O)— | —CH₃ |
| 129 | | —NH—C(=O)— | —NH—CH₂— | —CH₃ |

TABLE 7-continued

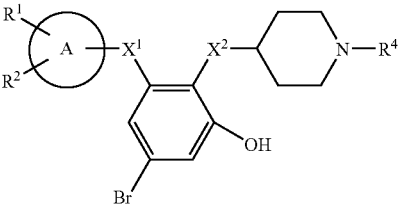

| No. | A (with R¹, R²) | X¹ | X² | R⁴ |
|---|---|---|---|---|
| 130 | | —NH—C(=O)— | —NH—CH₂— | —CH(CH₃)₂ |
| 131 | Br-pyridine-Me | —NH—C(=O)— | —NH—C(=O)— | —CH(CH₃)₂ |
| 132 | | —C(=O)—NH— | —NH—C(=O)— | —CH(CH₃)₂ |
| 133 | | —C(=O)—NH— | —NH—CH₂— | —CH(CH₃)₂ |
| 134 | | —NH—C(=O)— | —NH—C(=O)— | —CH(CH₃)₂ |
| 135 | F-pyridine-Me | —NH—C(=O)— | —NH—CH₂— | —CH(CH₃)₂ |
| 136 | | —C(=O)—NH— | —NH—C(=O)— | —CH(CH₃)₂ |
| 137 | | —C(=O)—NH— | —NH—CH₂— | —CH(CH₃)₂ |
| 138 | Me-pyridine-Me | —NH—C(=O)— | —NH—C(=O)— | —CH(CH₃)₂ |
| 139 | | —NH—C(=O)— | —NH—CH₂— | —CH(CH₃)₂ |
| 140 | MeO-pyridine-Me | —NH—C(=O)— | —NH—C(=O)— | —CH(CH₃)₂ |
| 141 | | —NH—C(=O)— | —NH—CH₂— | —CH(CH₃)₂ |
| 142 | Cl-pyridine-Me | —NH—C(=O)— | —NH—C(=O)— | —CH(CH₃)₂ |
|  | | —NH—C(=O)— | —NH—CH₂— | —CH(CH₃)₂ |
| 144 | | —NH—C(=O)— | —NH—C(=O)— | —CH(CH₃)₂ |
| 145 | Cl-thiazole-Me | —NH—C(=O)— | —NH—CH₂— | —CH(CH₃)₂ |
| 146 | | —C(=O)—NH— | —NH—C(=O)— | —CH(CH₃)₂ |
| 147 | | —C(=O)—NH— | —NH—CH₂— | —CH(CH₃)₂ |
| 148 | Cl-phenyl | —NH—C(=O)— | —NH—CH₂— | —CH(CH₃)₂ |
| 149 | | —C(=O)—NH— | —NH—CH₂— | —CH(CH₃)₂ |
| 150 | F-phenyl | —NH—C(=O)— | —NH—CH₂— | —CH(CH₃)₂ |
| 151 | | —C(=O)—NH— | —NH—CH₂— | —CH(CH₃)₂ |
| 152 | MeO-phenyl | —NH—C(=O)— | —NH—CH₂— | —CH(CH₃)₂ |
| 153 | | —C(=O)—NH— | —NH—CH₂— | —CH(CH₃)₂ |
| 154 | Me-phenyl | —NH—C(=O)— | —NH—CH₂— | —CH(CH₃)₂ |
| 155 | | —C(=O)—NH— | —NH—CH₂— | —CH(CH₃)₂ |
| 156 | FH₂C—O-phenyl | —NH—C(=O)— | —NH—CH₂— | —CH(CH₃)₂ |
| 157 | | —C(=O)—NH— | —NH—CH₂— | —CH(CH₃)₂ |
| 158 | F₂HC—O-phenyl | —NH—C(=O)— | —NH—CH₂— | —CH(CH₃)₂ |
| 159 | | —C(=O)—NH— | —NH—CH₂— | —CH(CH₃)₂ |

TABLE 7-continued

[Structure: Ring A with R¹, R² substituents connected via X¹ to a benzene ring (with OH and Br substituents) connected via X² to a piperidine ring with N—R⁴]

| No. | R¹/R²–A– | X¹ | X² | R⁴ |
|---|---|---|---|---|
| 160 | MeO-/F- phenyl | —NH—C(=O)— | —NH—CH₂— | —CH(CH₃)₂ |
| 161 | MeO-/F- phenyl | —C(=O)—NH— | —NH—CH₂— | —CH(CH₃)₂ |
| 162 | Cl-pyridazine | —NH—C(=O)— | —NH—C(=O)— | —CH(CH₃)₂ |
| 163 | Cl-pyridazine | —NH—C(=O)— | —NH—CH₂— | —CH(CH₃)₂ |
| 164 | Cl-pyridazine | —C(=O)—NH— | —NH—C(=O)— | —CH(CH₃)₂ |
| 165 | Cl-pyridazine | —C(=O)—NH— | —NH—CH₂— | —CH(CH₃)₂ |
| 166 | Cl-pyrimidine | —NH—C(=O)— | —NH—C(=O)— | —CH(CH₃)₂ |
| 167 | Cl-pyrimidine | —NH—C(=O)— | —NH—CH₂— | —CH(CH₃)₂ |
| 168 | Cl-pyrimidine | —C(=O)—NH— | —NH—C(=O)— | —CH(CH₃)₂ |
| 169 | Cl-pyrimidine | —C(=O)—NH— | —NH—CH₂— | —CH(CH₃)₂ |
| 170 | Cl-thiazole | —NH—C(=O)— | —NH—C(=O)— | —CH(CH₃)₂ |
| 171 | Cl-thiazole | —NH—C(=O)— | —NH—CH₂— | —CH(CH₃)₂ |
| 172 | Cl-thiazole | —C(=O)—NH— | —NH—C(=O)— | —CH(CH₃)₂ |
| 173 | Cl-oxazole | —NH—C(=O)— | —NH—C(=O)— | —CH(CH₃)₂ |
| 174 | Cl-oxazole | —NH—C(=O)— | —NH—CH₂— | —CH(CH₃)₂ |
| 175 | Cl-oxazole | —C(=O)—NH— | —NH—C(=O)— | —CH(CH₃)₂ |

TABLE 8

[Structure: Ring A with R¹, R² substituents connected via X¹ to a benzene ring (with OH, Y, Z substituents) connected via X² to a piperidine ring with N—CH(Me)₂]

| No. | R¹/R²–A– | X¹ | X² | Y | Z |
|---|---|---|---|---|---|
| 176 | Cl-pyridine | —NH—C(=O)— | —NH—C(=O)— | CN | H |
| 177 | Cl-pyridine | —NH—C(=O)— | —NH—CH₂— | CN | H |
| 178 | Cl-pyridine | —C(=O)—NH— | —NH—C(=O)— | CN | H |
| 179 | Cl-pyridine | —C(=O)—NH— | —NH—CH₂— | CN | H |
| 180 | MeO-phenyl | —NH—C(=O)— | —NH—CH₂— | CN | H |
| 181 | MeO-phenyl | —C(=O)—NH— | —NH—CH₂— | CN | H |

TABLE 8-continued

| No. | A (R¹, R²) | X¹ | X² | Y | Z |
|---|---|---|---|---|---|
| 182 | 5-Cl-pyridin-2-yl | —NH—C(=O)— | —NH—C(=O)— | Me | H |
| 183 | 5-Cl-pyridin-2-yl | —NH—C(=O)— | —NH—CH₂— | Me | H |
| 184 | 5-Cl-pyridin-2-yl | —C(=O)—NH— | —NH—C(=O)— | Me | H |
| 185 | 5-Cl-pyridin-2-yl | —C(=O)—NH— | —NH—CH₂— | Me | H |
| 186 | 4-MeO-phenyl | —NH—C(=O)— | —NH—CH₂— | Me | H |
| 187 | 4-MeO-phenyl | —C(=O)—NH— | —NH—CH₂— | Me | H |
| 188 | 5-Cl-pyridin-2-yl | —NH—C(=O)— | —NH—C(=O)— | H | Me |
| 189 | 5-Cl-pyridin-2-yl | —NH—C(=O)— | —NH—CH₂— | H | Me |
| 190 | 5-Cl-pyridin-2-yl | —C(=O)—NH— | —NH—C(=O)— | H | Me |
| 191 | 5-Cl-pyridin-2-yl | —C(=O)—NH— | —NH—CH₂— | H | Me |
| 192 | 4-MeO-phenyl | —NH—C(=O)— | —NH—CH₂— | H | Me |
| 193 | 4-MeO-phenyl | —C(=O)—NH— | —NH—CH₂— | H | Me |
| 194 | 5-Cl-pyridin-2-yl | —NH—C(=O)— | —NH—C(=O)— | —OMe | H |
| 195 | 5-Cl-pyridin-2-yl | —NH—C(=O)— | —NH—CH₂— | —OMe | H |
| 196 | 5-Cl-pyridin-2-yl | —C(=O)—NH— | —NH—C(=O)— | —OMe | H |
| 197 | 5-Cl-pyridin-2-yl | —C(=O)—NH— | —NH—CH₂— | —OMe | H |
| 198 | 4-MeO-phenyl | —NH—C(=O)— | —NH—CH₂— | —OMe | H |
| 199 | 4-MeO-phenyl | —C(=O)—NH— | —NH—CH₂— | —OMe | H |
| 200 | 5-Cl-pyridin-2-yl | —NH—C(=O)— | —NH—C(=O)— | CF₃ | H |
| 201 | 5-Cl-pyridin-2-yl | —NH—C(=O)— | —NH—CH₂— | CF₃ | H |
| 202 | 5-Cl-pyridin-2-yl | —C(=O)—NH— | —NH—C(=O)— | CF₃ | H |
| 203 | 5-Cl-pyridin-2-yl | —C(=O)—NH— | —NH—CH₂— | CF₃ | H |
| 204 | 4-MeO-phenyl | —NH—C(=O)— | —NH—CH₂— | CF₃ | H |
| 205 | 4-MeO-phenyl | —C(=O)—NH— | —NH—CH₂— | CF₃ | H |
| 206 | 5-Cl-pyridin-2-yl | —NH—C(=O)— | —NH—C(=O)— | OCF₃ | H |
| 207 | 5-Cl-pyridin-2-yl | —NH—C(=O)— | —NH—CH₂— | OCF₃ | H |
| 208 | 5-Cl-pyridin-2-yl | —C(=O)—NH— | —NH—C(=O)— | OCF₃ | H |
| 209 | 5-Cl-pyridin-2-yl | —C(=O)—NH— | —NH—CH₂— | OCF₃ | H |
| 210 | 4-MeO-phenyl | —NH—C(=O)— | —NH—CH₂— | OCF₃ | H |
| 211 | 4-MeO-phenyl | —C(=O)—NH— | —NH—CH₂— | OCF₃ | H |
| 212 | 5-Cl-pyridin-2-yl | —NH—C(=O)— | —NH—C(=O)— | NHSO₂Me | H |
| 213 | 5-Cl-pyridin-2-yl | —NH—C(=O)— | —NH—CH₂— | NHSO₂Me | H |
| 214 | 5-Cl-pyridin-2-yl | —C(=O)—NH— | —NH—C(=O)— | NHSO₂Me | H |
| 215 | 5-Cl-pyridin-2-yl | —C(=O)—NH— | —NH—CH₂— | NHSO₂Me | H |
| 216 | 4-MeO-phenyl | —NH—C(=O)— | —NH—CH₂— | NHSO₂Me | H |
| 217 | 4-MeO-phenyl | —C(=O)—NH— | —NH—CH₂— | NHSO₂Me | H |

TABLE 8-continued

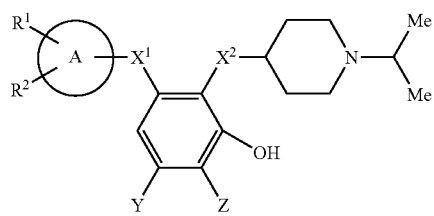

| No. | A (with R¹, R²) | X¹ | X² | Y | Z |
|---|---|---|---|---|---|
| 218 | 5-Cl-pyridin-2-yl | —NH—C(=O)— | —NH—C(=O)— | NHCOMe | H |
| 219 | 5-Cl-pyridin-2-yl | —NH—C(=O)— | —NH—CH₂— | NHCOMe | H |
| 220 | 5-Cl-pyridin-2-yl | —C(=O)—NH— | —NH—C(=O)— | NHCOMe | H |
| 221 | 5-Cl-pyridin-2-yl | —C(=O)—NH— | —NH—CH₂— | NHCOMe | H |
| 222 | 4-MeO-phenyl | —NH—C(=O)— | —NH—CH₂— | NHCOMe | H |
| 223 | 4-MeO-phenyl | —C(=O)—NH— | —NH—CH₂— | NHCOMe | H |
| 224 | 5-Cl-pyridin-2-yl | —NH—C(=O)— | —NH—C(=O)— | C(=O)Me | H |
| 225 | 5-Cl-pyridin-2-yl | —NH—C(=O)— | —NH—CH₂— | C(=O)Me | H |
| 226 | 5-Cl-pyridin-2-yl | —C(=O)—NH— | —NH—C(=O)— | C(=O)Me | H |
| 227 | 5-Cl-pyridin-2-yl | —C(=O)—NH— | —NH—CH₂— | C(=O)Me | H |
| 228 | 4-MeO-phenyl | —NH—C(=O)— | —NH—CH₂— | C(=O)Me | H |
| 229 | 4-MeO-phenyl | —C(=O)—NH— | —NH—CH₂— | C(=O)Me | H |
| 230 | 5-Cl-pyridin-2-yl | —NH—C(=O)— | —NH—C(=O)— | COOMe | H |
| 231 | 5-Cl-pyridin-2-yl | —NH—C(=O)— | —NH—CH₂— | COOMe | H |
| 232 | 5-Cl-pyridin-2-yl | —C(=O)—NH— | —NH—C(=O)— | COOMe | H |
| 233 | 5-Cl-pyridin-2-yl | —C(=O)—NH— | —NH—CH₂— | COOMe | H |
| 234 | 4-MeO-phenyl | —NH—C(=O)— | —NH—CH₂— | COOMe | H |
| 235 | 4-MeO-phenyl | —C(=O)—NH— | —NH—CH₂— | COOMe | H |
| 236 | 5-Cl-pyridin-2-yl | —NH—C(=O)— | —NH—C(=O)— | CONH₂ | H |
| 237 | 5-Cl-pyridin-2-yl | —C(=O)—NH— | —NH—CH₂— | CONH₂ | H |
| 238 | 5-Cl-pyridin-2-yl | —NH—C(=O)— | —NH—C(=O)— | SMe | H |
| 239 | 5-Cl-pyridin-2-yl | —C(=O)—NH— | —NH—CH₂— | SMe | H |
| 240 | 5-Cl-pyridin-2-yl | —NH—C(=O)— | —NH—C(=O)— | I | H |
| 241 | 5-Cl-pyridin-2-yl | —C(=O)—NH— | —NH—CH₂— | I | H |

TABLE 9
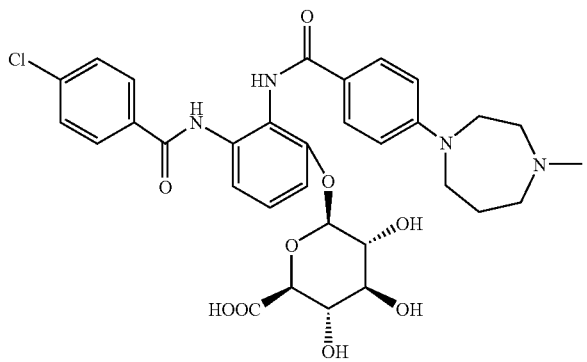
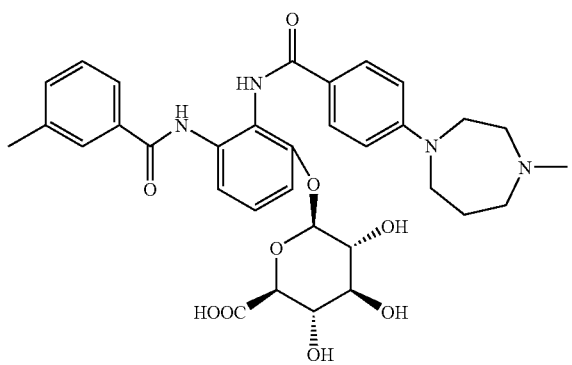
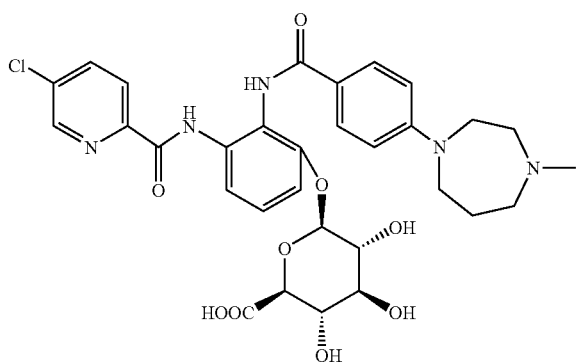
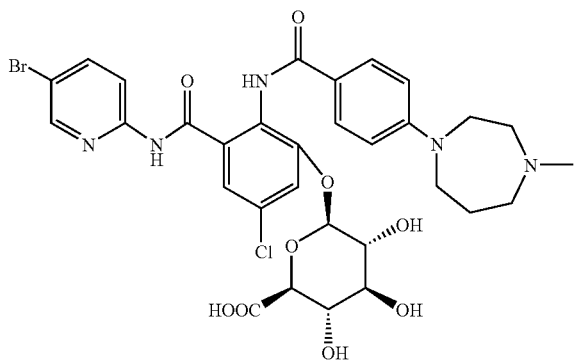

TABLE 9-continued
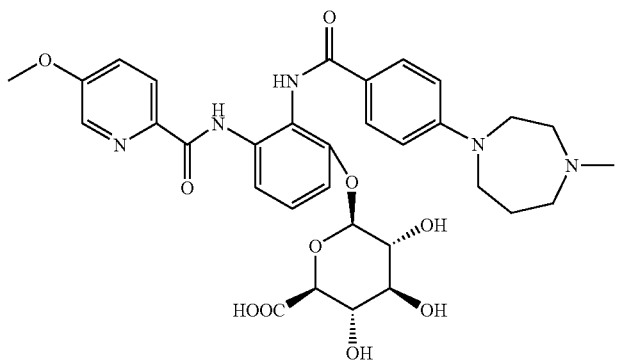
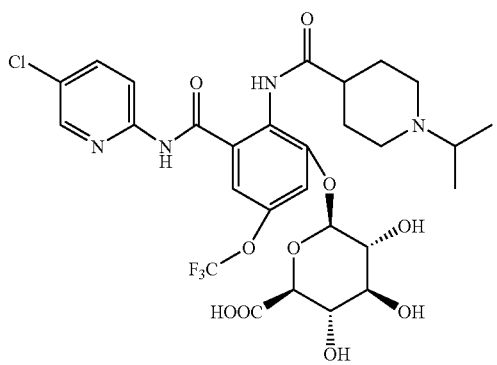
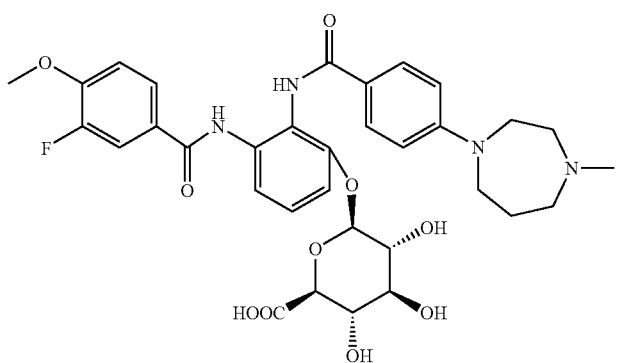
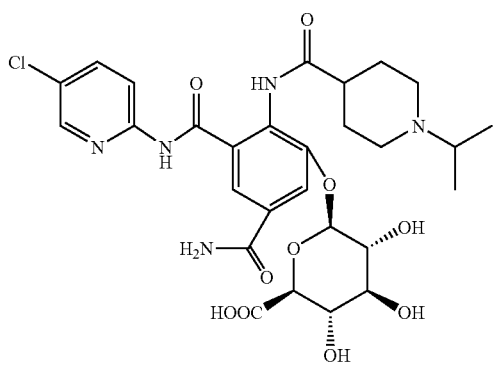

TABLE 9-continued
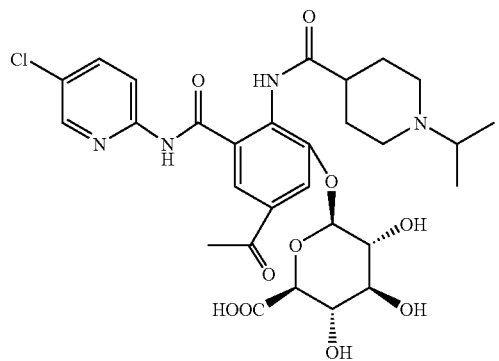
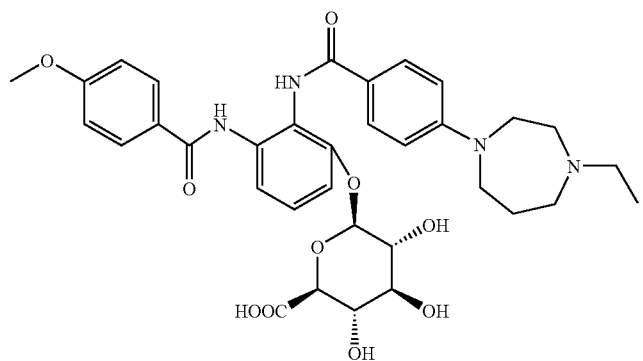
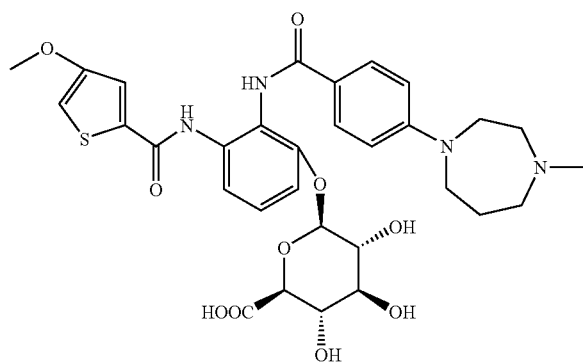
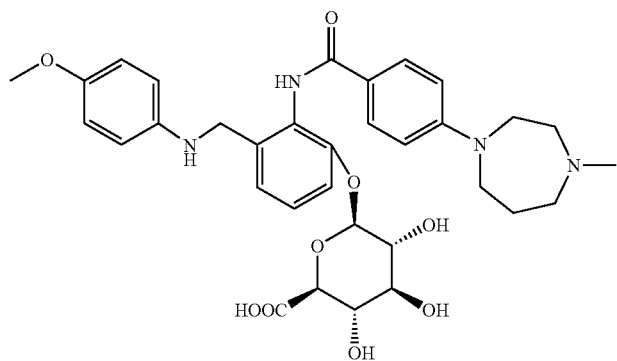

TABLE 9-continued
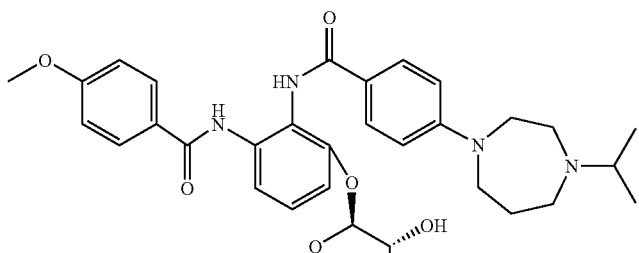
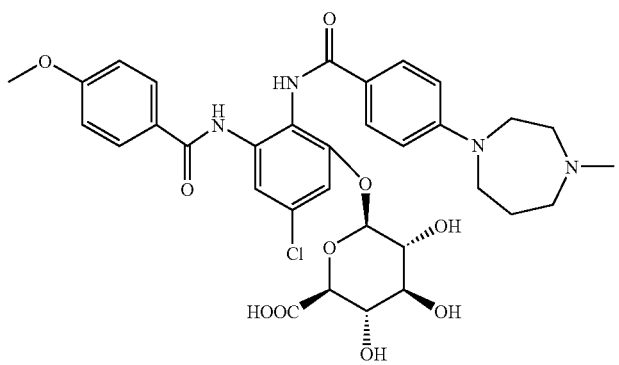
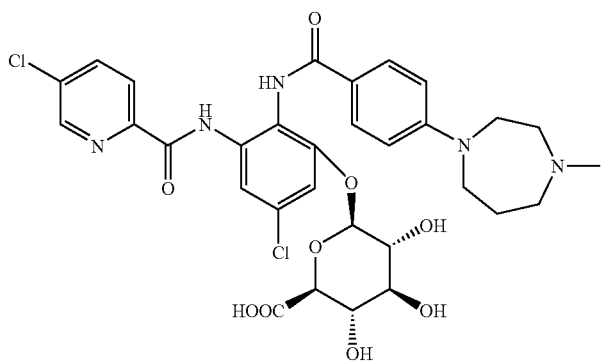
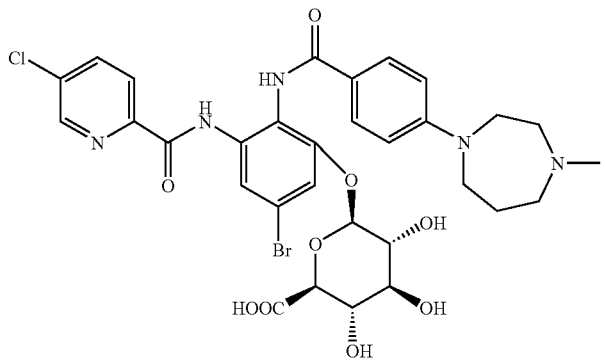

TABLE 9-continued
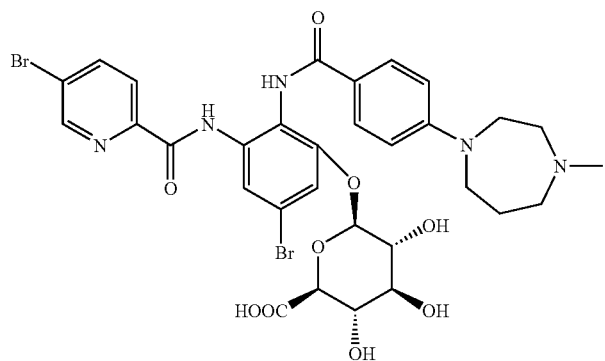
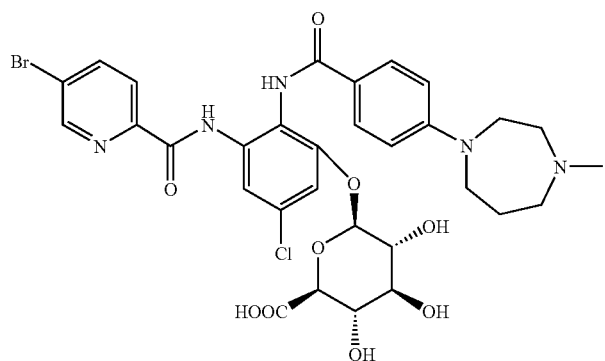
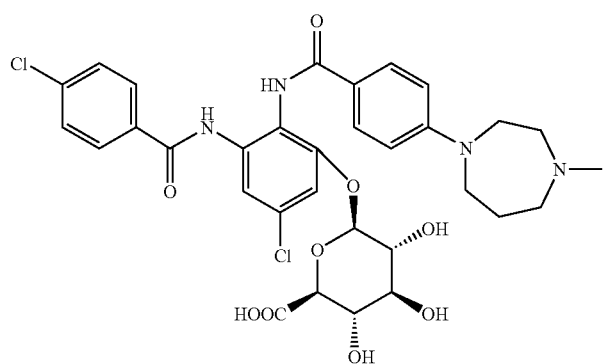
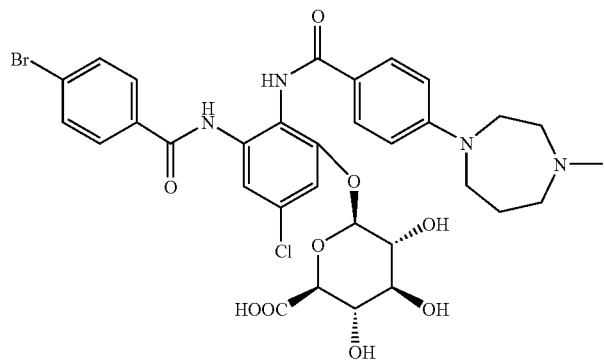

TABLE 9-continued
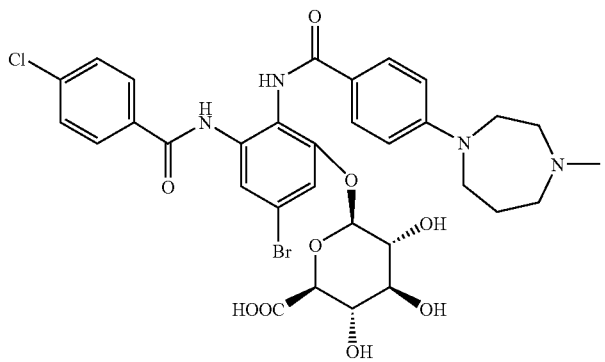
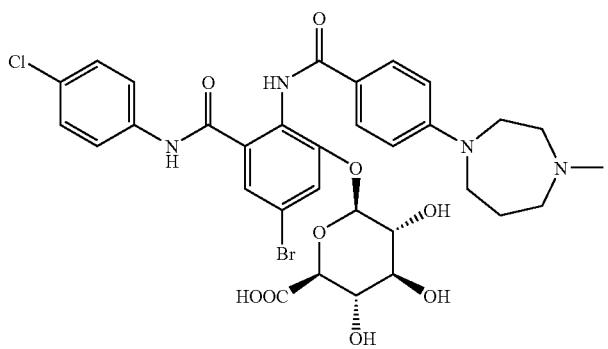
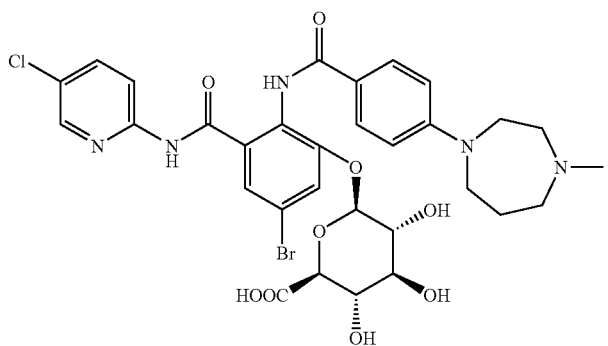
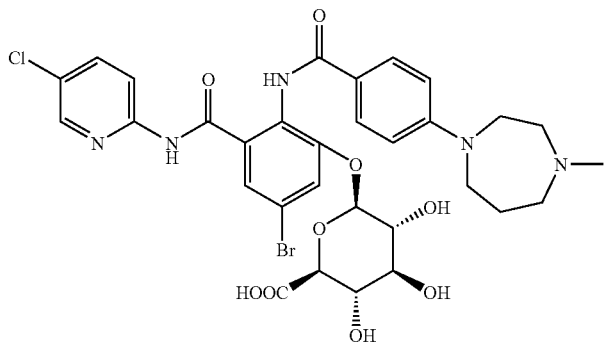

TABLE 9-continued
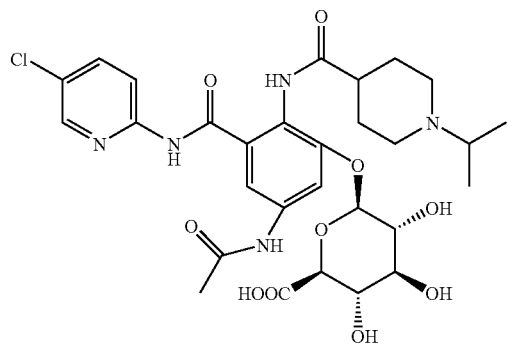
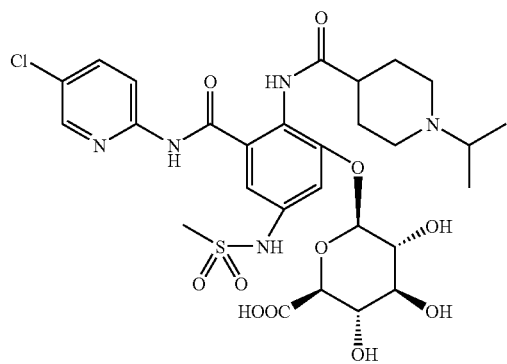
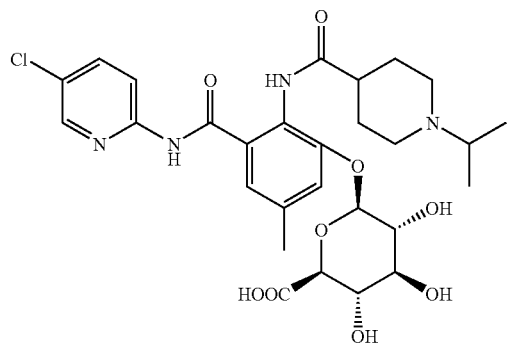
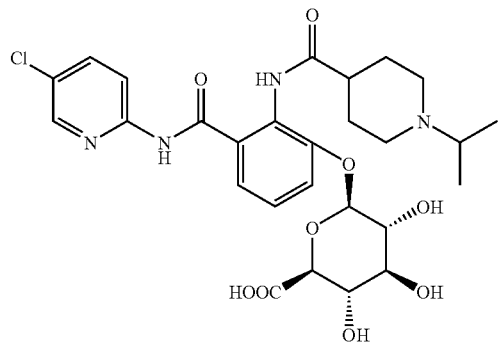

TABLE 9-continued
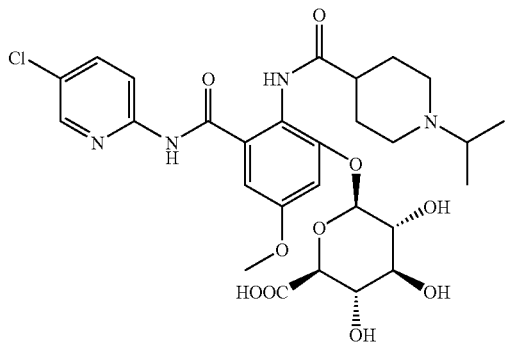
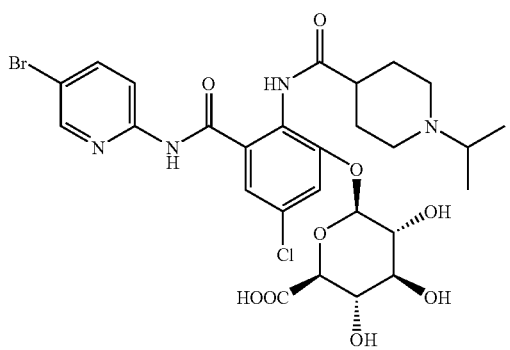
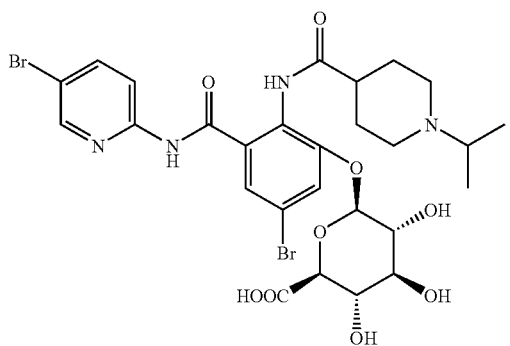
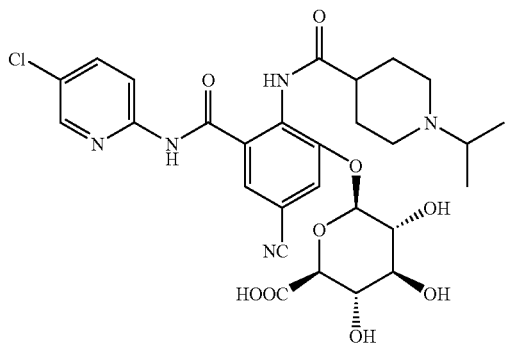

TABLE 9-continued
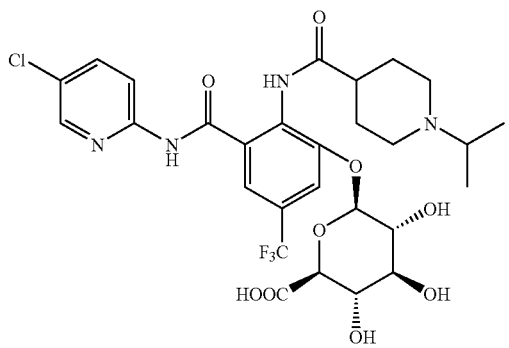
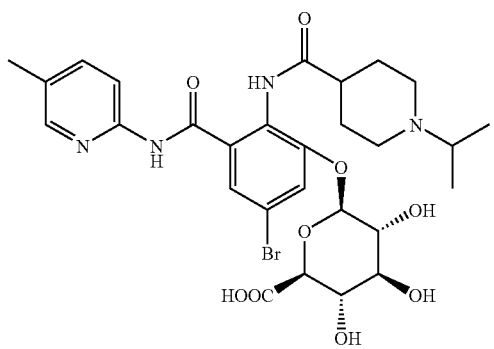
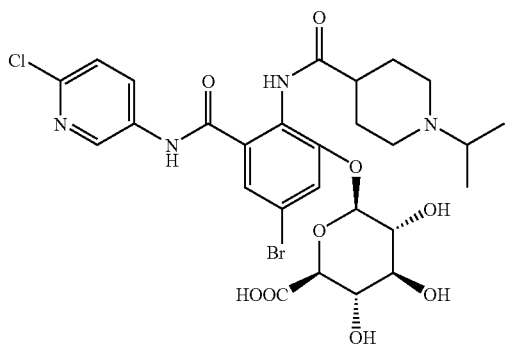
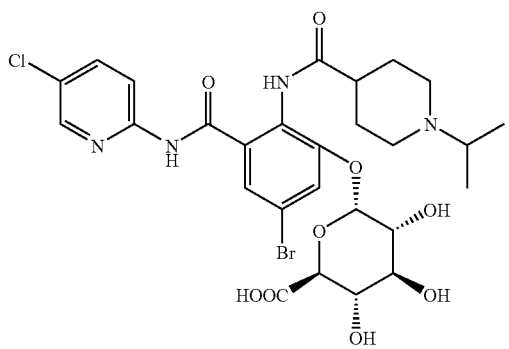

TABLE 9-continued
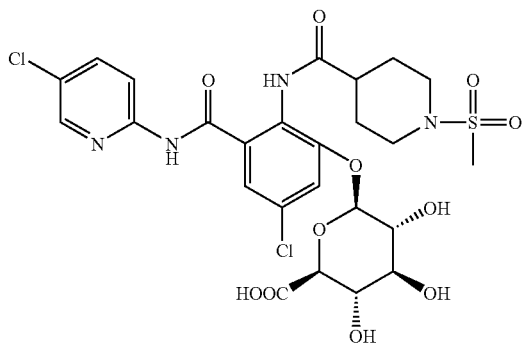
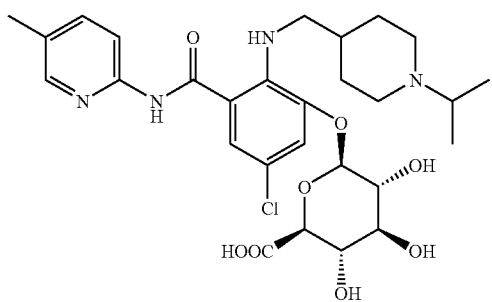
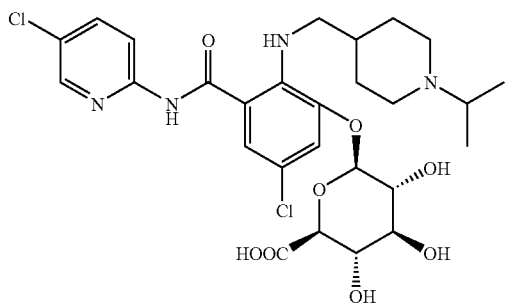
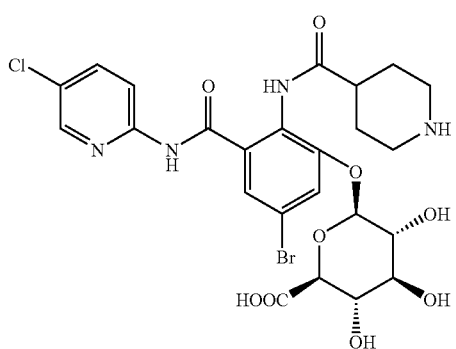
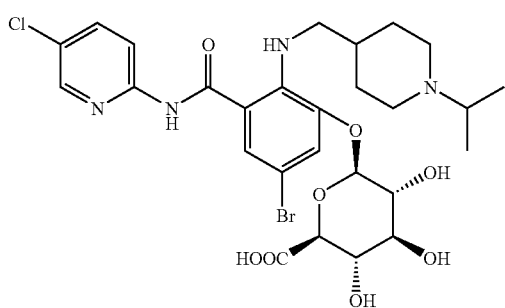

TABLE 9-continued

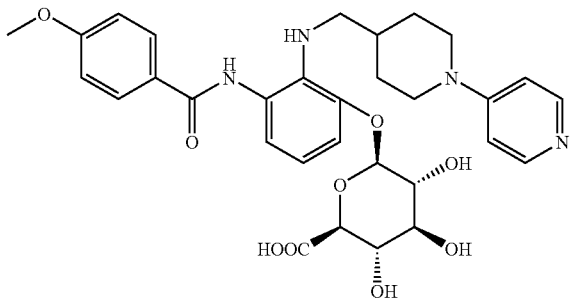

The invention claimed is:

1. The compound 4'-chloro-2'-[(5-chloro-2-pyridyl)carbamoyl]-6'-hydroxy-1-isopropylpiperidine-4-carboxanilide or a salt thereof.

2. The compound 4'-bromo-2'-[(5-chloro-2-pyridyl)carbamoyl]-6'-hydroxy-1-isopropylpiperidine-4-carboxanilide or a salt thereof.

3. The compound 2'-[(5-bromo-2-pyridyl)carbamoyl]-4'-chloro-6'-hydroxy-1-isopropylpiperidine-4-carboxanilide or a salt thereof.

4. The compound 5-chloro-N-(5-chloro-2-pyridyl)-3-hydroxy-2-{[(1-isopropyl-4-piperidyl)methyl]amino}benzamide or a salt thereof.

5. The compound N-(5-bromo-2-pyridyl)-5-chloro-3-hydroxy-2-{[(1-isopropyl-4-piperidyl)methyl]amino}benzamide or a salt thereof.

6. A pharmaceutical composition where the compound mentioned in claim 1, 2, 3, 4 or 5 or a salt thereof is an effective ingredient.

7. The pharmaceutical composition according to claim 6 wherein it is an activated blood coagulation factor X inhibitor.

* * * * *